(12) United States Patent
Chen et al.

(10) Patent No.: US 7,517,663 B2
(45) Date of Patent: Apr. 14, 2009

(54) RABBIT MONOCLONAL ANTIBODY AGAINST ID1 PROTEIN

(75) Inventors: Jung-Shou Chen, Foster City, CA (US); William A. Garland, San Clemente, CA (US)

(73) Assignees: Biocheck, Inc., Foster City, CA (US); Angiogenex, Inc., New York, NY (US)

( * ) Notice: Subject to any disclaimer, the term of this patent is extended or adjusted under 35 U.S.C. 154(b) by 323 days.

(21) Appl. No.: 11/453,156

(22) Filed: Jun. 13, 2006

(65) Prior Publication Data

US 2006/0286609 A1 Dec. 21, 2006

Related U.S. Application Data

(60) Provisional application No. 60/691,060, filed on Jun. 16, 2005.

(51) Int. Cl.
| | |
|---|---|
| *C07K 16/30* | (2006.01) |
| *C12N 5/18* | (2006.01) |
| *G01N 33/53* | (2006.01) |
| *G01N 33/543* | (2006.01) |
| *G01N 33/574* | (2006.01) |
| *C07H 21/04* | (2006.01) |
| *C12P 21/08* | (2006.01) |

(52) U.S. Cl. .................. 435/7.94; 435/7.1; 435/7.23; 435/7.92; 435/7.93; 435/7.95; 435/40.52; 435/70.21; 435/326; 435/332; 435/344; 436/503; 436/518; 436/548; 436/64; 530/388.2; 530/388.8; 530/391.1; 536/23.53

(58) Field of Classification Search .................. 435/7.1, 435/7.2, 7.23, 7.92, 7.93, 7.94, 7.95, 40.52, 435/70.21, 326, 332, 344; 436/503, 518, 436/547, 548, 64; 530/388.2, 388.8, 391.1; 536/23.53

See application file for complete search history.

(56) References Cited

U.S. PATENT DOCUMENTS 5,675,063 A * 10/1997 Knight ..................... 800/14
7,267,951 B2 * 9/2007 Alani et al. ................. 435/6

OTHER PUBLICATIONS

Harlow et al., 1988. Antibodies. A Laboratory Manual, Cold Spring Harbor Laboratory, Cold Spring Harbor. pp. 72-77.*
Campbell, 1984. Monoclonal Antibody Technology, Elsevier, Amsterdam. pp. 1-4 and 29.*
Zhu et al., 1995. Id gene expression during development and molecular cloning of the human Id-1 gene. Molecular Brain Res. 30: 312-326.*
Lin et al., 2000. A role for Id-1 in the aggressive phenotype and steroid hormone response of human breast cancer cells. Cancer Res. 60: 1332-1340.*
Uehara et al., 2003. Id-1 is not expressed in the luminal epithelial cells of mammary glands. Breast Cancer Res. 5: R25-R29.*
Schaefer et al., 2001. Expression of the helix-loop-helix protein ID1 in keratinocytes is upregualted by loss of cell-matrix contact. Exp. Cell Res. 266: 250-259.*

* cited by examiner

*Primary Examiner*—James L Grun
(74) *Attorney, Agent, or Firm*—Howrey LLP; Viola T. Kung

(57) ABSTRACT

The present invention relates to a rabbit monoclonal antibody that binds to human Id1 protein and/or mouse Id1 protein with high specificity and high affinity. The antibody has a binding constant, measured with respect to human Id1 protein and/or mouse Id1 protein, equal to or greater than $1 \times 10^8$/molar. The antibody has no substantial cross-reactivity with other family Id proteins such as Id2, Id3, or Id4, or other endogenous proteins present in the cells that express Id1 protein. The high specificity and high affinity of the rabbit monoclonal antibodies of the present invention allows sensitive and specific detection and/or quantitation of Id1 protein in biological samples. The antibodies are useful in immunochemical-based assays such as ELISA, western blot, and immunohistochemical staining.

13 Claims, 7 Drawing Sheets
(2 of 7 Drawing Sheet(s) Filed in Color)

A. BioCheck Rabbit Monoclonal Anti-Human Id1 (Clone #BCH-2/#5-3) (1:50)

B. Santa Cruz Rabbit Polyclonal Anti-Mouse/Human Id1 (1:200)

RABBIT MONOCLONAL ANTIBODY AGAINST ID1 PROTEIN

This application claims priority to U.S. provisional application No. 60/691,060, filed Jun. 16, 2005. The content of which is incorporated herein by reference in its entirety.

FIELD OF THE INVENTION

The field of this invention relates to rabbit monoclonal antibodies against human Id1 protein and/or mouse Id1 protein and the use of these antibodies in immunochemical-based assays to detect and/or quantitate Id1 proteins in biological samples.

BACKGROUND OF THE INVENTION

The Id proteins are a family of four related proteins implicated in the control of differentiation and cell cycle progression in organisms ranging from flies to man [Ruzinova et al., Trends Cell Biol; 13:410-418, (2003), Hasskarl et al., Cancer Biol Ther; 1:91-6, (2002), Lasorella et al., Oncogene; 20:8326-33 (2001), Sikder et al., Cancer Cell; 3:525-30 (2003), Fong et al., Trends Mol Med; 10: 387-92 (2004) and Zebedee and Hara, Oncogene; 20: 8317-25(2001)]. The four Id proteins, Id1, Id2, Id3 and Id4, affect control by sequestering basic helix-loop-helix (bHLH) transcription factors and forming heterodimers that are unable to bind to DNA [Benezra et al., Cell, 61:49-59 (1990), O'Toole et al., J Biol Chem; 278: 45770-62003 (2003), Lister and Baron, Gene Expr; 7: 25-38 (1998) and Yates et al., Embo J; 18:968-76 (1999)]. In this regard, biochemical and genetic data have established that the target of the Id proteins are the ubiquitously expressed bHLH proteins referred to as E proteins such as E12, E47, E2-2 and HEB as well as certain tissue-restricted HLH proteins such as MyoD, MRFs, etc., that control cell type specific gene expression and the expression of cell cycle regulatory genes [Lassar et al., Curr Opin Cell Biol; 6:788-94 (1994) and Langlands et al., J Biol Chem; 272: 19785-93 (1997)]. The structural mediator of this sequestering process is a highly conserved dimerization motif known as the helix-loop-helix (HLH) domain that is common to all four proteins [Riechmann et al., Nucleic Acids Res; 22:749-55 (1994) and Langlands et al., J Biol Chem; 272: 19785-93 (1997)]. The bHLH proteins contain a cluster of amino acids rich in basic residues adjacent to the HLH dimerization motif which mediates DNA binding of homodimeric or heterodimeric HLH complexes. Since the Id proteins lack a basic DNA binding domain, the heterodimers between Id and bHLH proteins cannot bind DNA. This dominant negative mode of inhibition of DNA binding activity is widely used in the cell and is also employed by members of the leucine zipper and homeodomain protein families [Ron and Habener, Genes Dev; 6: 439-453 (1992)].

Id1 and Id3 are co-expressed temporally and spatially during mouse neurogenesis and in tissues undergoing active morphogenesis [Duncan et al., Dev. Biol; 154:1-10 (1992), Ellmeier, et al., Dev Dyn; 203:163-73 (1995) and Jen, Y., et al., Dev Dyn; 208:92-106 (1997)]. Id1 and Id3 are also important to neovascularization, a process important to the growth, progression and metastasis of tumors [Dhanabal et al., Curr. Med. Chem. Anticancer Agents; 5: 115-30 (2005) and Ferrara et al., Nat Rev Drug Discov; 3: 391-400 (2004)]. The loss of the Id1 and Id3 genes (knockout mouse) results in impaired neovascularization and diminished ability to support tumor growth in animals [Lyden et al., Nature, 401:670-7 (1999) and Lyden et al., Nat Med; 7: 1194-201 (2001)]. Consistent with this observed anti-tumor activity, the regulation of many biochemicals important to angiogenesis like MMP2 and certain integrins are influenced by Id proteins [Lyden et al., Nature, 401:670-7 (1999) and Ruzinova et al., Cancer Cell; 4: 277-89 (2003)].

Breast cancer is one of many pathologies illustrating the important role of Id genes and proteins in promoting cell proliferation and negatively regulating differentiation [de Candia et al., Adv Cancer Res; 92: 81-94 (2004), Coletta et al., J Mammary Gland Biol Neoplasia; 9: 39-53 (2004), Desprez et al., J Mammary Gland Biol Neoplasia; 8: 225-39 (2003) and Fong et al., Proc Natl Acad Sci USA; 100: 13543-8 (2003)]. High levels of Id gene expression have also been observed in tumor cell lines derived from different tissues. In accordance with this, one of the members of this gene family, Id1, has been shown to promote proliferation and inhibit functional differentiation of mouse mammary epithelial cells (SCp2 cells), maintained in cell culture [Desprez et al., Mol Cell Biol, 15:3398-3404 (1995)]. In addition, Id1 deletion totally blocks tumor formation in an animal model of human breast cancer when combined with treatment with an HSP-90 inhibitor [de Candia P et al., Proc Natl Acad Sci USA; 100: 12337-42 (2003)]. Experiments establishing the role of particular Id proteins in a specific type of cancer are heavily dependent on analysis by immunohistochemistry (IHC) of specific tumor samples. For example, normal mammary gland is composed of several cell types, but it is the luminal epithelial cells, which line the inside of ducts and the lobules, that are primarily targeted for proliferation, differentiation and carcinogenesis. Therefore, to assess the precise significance of any regulatory factor in mammary biology and its significance to carcinogenesis, it is essential to examine its cellular localization in vivo. This is particularly important in the case of ubiquitously expressed proteins, such as Id proteins. In this regard, an examination of the in situ localization of Id1 in normal mammary glands reported that Id1 is not expressed in the luminal epithelial cells.

The work defining the role of Id1 in cancers such as breast cancer is limited by the lack of antibodies with suitable sensitivity and specificity to Id1. Sensitivity is an important characteristic for an antibody to detect and/or quantitate Id1, which is very potent and is present in biologic systems at low concentrations [Langlands et al., J Biol Chem; 272: 19785-19793 (1997)]

Production of monoclonal antibodies to the Id1 is difficult because of the relatively low molecular weight (about 17 kDa) and common structural homology among the Id proteins [Nagata and Todokoro, BioChem Biophys Res Commun; 30: 1355-1362 (1994) and Andres-Barquin et al., Histol Histopathol; 15; 603-618 (2000)]. Commercial rabbit polyclonal anti-mouse/human Id1 antibody (Santa Cruz Biotechnology, Santa Cruz, Calif.), and commercial mouse monoclonal anti-mouse Id1 antibody (BD PharMingen Corp., San Diego, Calif.) do not have desired binding specificity since it has cross-reactivity with other proteins and does not have high affinity to Id1. The undesired cross-reactivity and low binding affinity make the commercial antibodies unsuitable for use in immunoassays to detect Id1. It is also difficult to prepare polyclonal antibodies specific only to human Id1, with no cross-reactivity to mouse Id1; or specific only to mouse Id1, with no cross-reactivity to human Id1 because of the homology between mouse Id1 and human Id1.

There is a need for antibodies specific for Id1, which do not substantially cross-react with other endogenous proteins or those within the Id family proteins such as Id1, Id2, and Id4. There is also a need for antibodies that have high affinity to Id1 such that they are sensitive to detect or quantitate Id1 in biological samples. There is further a need for antibodies that are specific only to mouse Id1 or specific only to human Id1 with no substantial cross-reactivity between the two species.

REFERENCES

1. Andres-Barquin P J, Hernandez M C, Israel M A, Id genes in nervous system development, Histol Histopathol 2000; 15: 603-18.
2. Ball H J, Finlay D, Diagnostic application of monoclonal antibody (MAb)-based sandwich ELISAs, Methods Mol Biol 1998; 104: 127-32.
3. Benezra R, Davis R L, Lockshon D, Turner D L, Weintraub H, The protein Id: a negative regulator of helix-loop-helix DNA binding proteins, Cell 1990; 61: 49-59.
4. Coletta R D, Jedlicka P, Gutierrez-Hartmann A, Ford H L, Transcriptional control of the cell cycle in mammary gland development and tumorigenesis, J Mammary Gland Biol Neoplasia. January 2004; 9(1):39-53.
5. de Candia P, Benezra R, Solit D B, A role for Id proteins in mammary gland physiology and tumorigenesis, Adv Cancer Res 2004; 92: 81-94.
6. de Candia P, Solit D B, Giri D, Brogi E, Siegel P M, Olshen A B, Muller W J, Rosen N, Benezra R, Angiogenesis impairment in Id-deficient mice cooperates with an Hsp90 inhibitor to completely suppress HER2/neu-dependent breast tumors, Proc Natl Acad Sci USA 2003; 100: 12337-42.
7. Desprez P Y, Sumida T, Coppe J P, Helix-loop-helix proteins in mammary gland development and breast cancer, J Mammary Gland Biol Neoplasia 2003; 8: 225-39.
8. Desprez P Y, Hara E, Bissell M J, Campisi J, Suppression of mammary epithelial cell differentiation by the helix-loop-helix protein Id-1, Mol Cell Biol 1995; 15: 3398-404.
9. Dhanabal M, Jeffers M, Larochelle W J, Anti-angiogenic therapy as a cancer treatment paradigm, Curr Med Chem Anti-Canc Agents 2005; 5: 115-30.
10. Duncan M, DiCicco-Bloom E M, Xiang X, Benezra R, Chada K, The gene for the helix-loop-helix protein, Id, is specifically expressed in neural precursors, Dev Biol 1992; 154: 1-10.
11. Dykes D J, Abbott B J, Mayo J G, Harrison S D, Laster W R, Simpson-Herren L, Griswold D P, Development of human xenografts models for in vivo evaluation of new tumor drugs, Contrib Oncol Basel, Karger, 1992, Vol 42, pp 1-22.
12. Ellmeier W, Weith A, Expression of the helix-loop-helix gene Id3 during murine embryonic development, Dev Dyn 1995; 203: 163-73.
13. Ferrara N, Hillan K J, Gerber H P, Novotny W, Discovery and development of bevacizumab, an anti-VEGF antibody for treating cancer, Nat Rev Drug Discov 2004; 3: 391-400.
14. Fong S, Debs R J, Desprez P Y, Id genes and proteins as promising targets in cancer therapy, Trends Mol Med 2004; 10: 387-92.
15. Fong S, Itahana Y, Sumida T, Singh J, Coppe J P, Liu Y, Richards P C, Bennington J L, Lee N M, Debs R J, Desprez P Y, Id-1 as a molecular target in therapy for breast cancer cell invasion and metastasis, Proc Natl Acad Sci USA 2003; 100: 13543-8.
16. Hasskarl J, Munger K, Id proteins—tumor markers or oncogenes? Cancer Biol Ther 2002; 1: 91-6.
17. Jen Y, Manova K, Benezra R, Each member of the Id gene family exhibits a unique expression pattern in mouse gastrulation and neurogenesis, Dev Dyn 1997; 208: 92-106.
18. Langlands K, Yin X, Anand G, Prochownik E V, Differential interactions of Id proteins with basic-helix-loop-helix transcription factors, J Biol Chem 1997; 272: 19785-19793.
19. Lasorella A, Uo T, Iavarone A, Id proteins at the crossroad of development and cancer.
20. Oncogene 2001; 20: 8326-33.
21. Lassar A B, Skapek S X, Novitch B, Regulatory mechanisms that coordinate skeletal muscle differentiation and cell cycle withdrawal, Curr Opin Cell Biol 1994; 6: 788-94.
22. Lister J A, Baron M H, Induction of basic helix-loop-helix protein-containing complexes during erythroid differentiation, Gene Expr 1998; 7: 25-38.
23. Lyden D, Hattori K, Dias S, Costa C, Blaikie P, Butros L, Chadbum A, Heissig B, Marks W, Witte L, Wu Y, Hicklin D, Zhu Z, Hackett N R, Crystal R G, Moore M A, Hajjar K A, Manova K, Benezra R, Rafii S, Impaired recruitment of bone-marrow-derived endothelial and hematopoietic precursor cells blocks tumor angiogenesis and growth, Nat Med 2001; 7: 1194-201.
24. Lyden D, Young A Z, Zagzag D, Yan W, Gerald W, O'Reilly R, Bader B L, Hynes R O, Zhuang Y, Manova K, Benezra R, Id1 and Id3 are required for neurogenesis, angiogenesis and vascularization of tumour xenografts, Nature 1999; 401: 670-7.
25. Nagata Y, Todokoro K, Activation of helix-loop-helix proteins Id1, Id2 and Id3 during neural differentiation, Biochem Biophys Res Commun 1994; 199: 1355-62.
26. O'Toole P J, Inoue T, Emerson L, Morrison I E, Mackie A R, Cherry R J, Norton J D, Id proteins negatively regulate basic helix-loop-helix transcription factor function by disrupting subnuclear compartmentalization, J Biol Chem 2003; 278: 45770-45776.
27. Riechmann V, van Cruchten I, Sablitzky F, The expression pattern of Id4, a novel dominant negative helix-loop-helix protein, is distinct from Id1, Id2 and Id3, Nucleic Acids Res 1994; 22: 749-55.
28. Ron D, Habener J F, CHOP, a novel developmentally regulated nuclear protein that dimerizes with transcription factors C/EBP and LAP and functions as a dominant-negative inhibitor of gene transcription, Genes Dev 1992; 6: 439-53.
29. Ruzinova M B, Schoer R A, Gerald W, Egan J E, Pandolfi P P, Rafii S, Manova K, Mittal V, Benezra R, Effect of angiogenesis inhibition by Id loss and the contribution of bone-marrow-derived endothelial cells in spontaneous murine tumors, Cancer Cell 2003; 4:277-89.
30. Ruzinova M B, Benezra R, Id proteins in development, cell cycle and cancer, Trends Cell Biol 2003; 13: 410-8.
31. Sikder H A, Devlin M K, Dunlap S, Ryu B, Alani R M, Id proteins in cell growth and tumorigenesis, Cancer Cell. 2003; 3: 525-30.
32. Spieker-Polet H, Sethupathi P, Yam P C, Knight K L, Rabbit monoclonal antibodies: generating a fusion partner to produce rabbit-rabbit hybridomas, Proc Natl Acad Sci USA 1995; 92: 9348-52.
33. Sun X H, Baltimore D, Correction: an inhibitory domain of E12 transcription factor prevents DNA binding in E12 homodimers but not in E12 heterodimers, Cell. 1991; 66: 423.
34. Sun X H, Copeland N G, Jenkins N A, Baltimore D, Id proteins Id1 and Id2 selectively inhibit DNA binding by one class of helix-loop-helix proteins, Mol Cell Biol 1991; 11: 5603-5611.
35. Yates P R, Atherton G T, Deed R W, Norton J D, Sharrocks A D, Id helix-loop-helix proteins inhibit nucleoprotein complex formation by the TCF ETS-domain transcription factors, EMBO J. 1999; 18: 968-76.
36. Zebedee Z, Hara E, Id proteins in cell cycle control and cellular senescence, Oncogene. 2001; 20: 8317-25.

SUMMARY OF THE INVENTION

The present invention is directed to a rabbit monoclonal antibody that binds to human Id1 and/or mouse Id1 protein with high specificity and high affinity. The antibody has a binding constant, measured with respect to human Id1 protein or mouse Id1 protein, of equal to or greater than $1 \times 10^8$/molar, preferably $1 \times 10^9$, more preferably $1 \times 10^{10}$, more preferably $1 \times 10^{11}$, more preferably $1 \times 10^{12}$, and most preferably $1 \times 10^{13}$. The antibody has no substantial cross-reactivity to other family Id proteins such as Id2, Id3, or Id4, or other endogenous proteins present in the cells that express Id1 protein.

In one embodiment of the invention, the rabbit monoclonal antibodies only have reactivity toward human Id1 protein and have no substantial reactivity toward mouse Id1 protein. In another embodiment of the invention, the rabbit monoclonal antibodies only have reactivity toward mouse Id1 protein and have no substantial reactivity toward human Id1 protein. In a further embodiment of the invention, the rabbit monoclonal antibodies have substantial reactivity toward both human Id1 and mouse Id1 protein.

The specificity and high affinity of the rabbit monoclonal antibodies of the present invention allows sensitive and specific detection and quantitation of Id1 protein in biological samples. The antibodies are useful in immunochemical-based assays such as ELISA, western blot, and immunohistochemical staining. The antibodies provide a tool for sensitive and accurate detection of a disease, which results in the overproduction of Id1 such as breast cancer and other cancers. The antibodies also provide a tool for assess Id1 levels in various experimental biologic test systems.

BRIEF DESCRIPTION OF THE DRAWINGS

This application file contains at least one drawing executed in color. Copies of this patent or patent application publication with color drawing(s) will be provided by the Office upon request and payment of the necessary fee.

FIGS. 2-1A and 2-1B are Western blot analysis of extracts from HeLa cells. Extracts in the (−) lanes are from untransfected cells that express human Id1. Extracts in the (+) lane are cells transfected to express both mouse Id1 and human Id1. The rabbit monoclonal anti-human Id1, clone #BCH-2/#5-3, of this invention was used to develop blots A. Santa Cruz Biotechnology's rabbit polyclonal anti-mouse/human Id1 was used to develop blot B. In these blots the molecular weight markers are in kDa, and the MW of Id1, ~15 kDa, is designated with **.

FIG. 2-2A and 2-2B are is Western blot analysis of extracts from breast cancer (468, 231, 435), melanoma (A2058, A375P, HT144), and cervical carcinoma (SiHa and HeLa). The rabbit monoclonal anti-human Id1, clone #BCH-2/#5-3, of this invention was used to develop blots A. Santa Cruz Biotechnology's rabbit polyclonal anti-mouse/human Id1 was used to develop blot B. In these blots,the MW of Id1, ~15 kDa, is designated with **.

DETAILED DESCRIPTION OF THE INVENTION

Definitions

Figure 1:
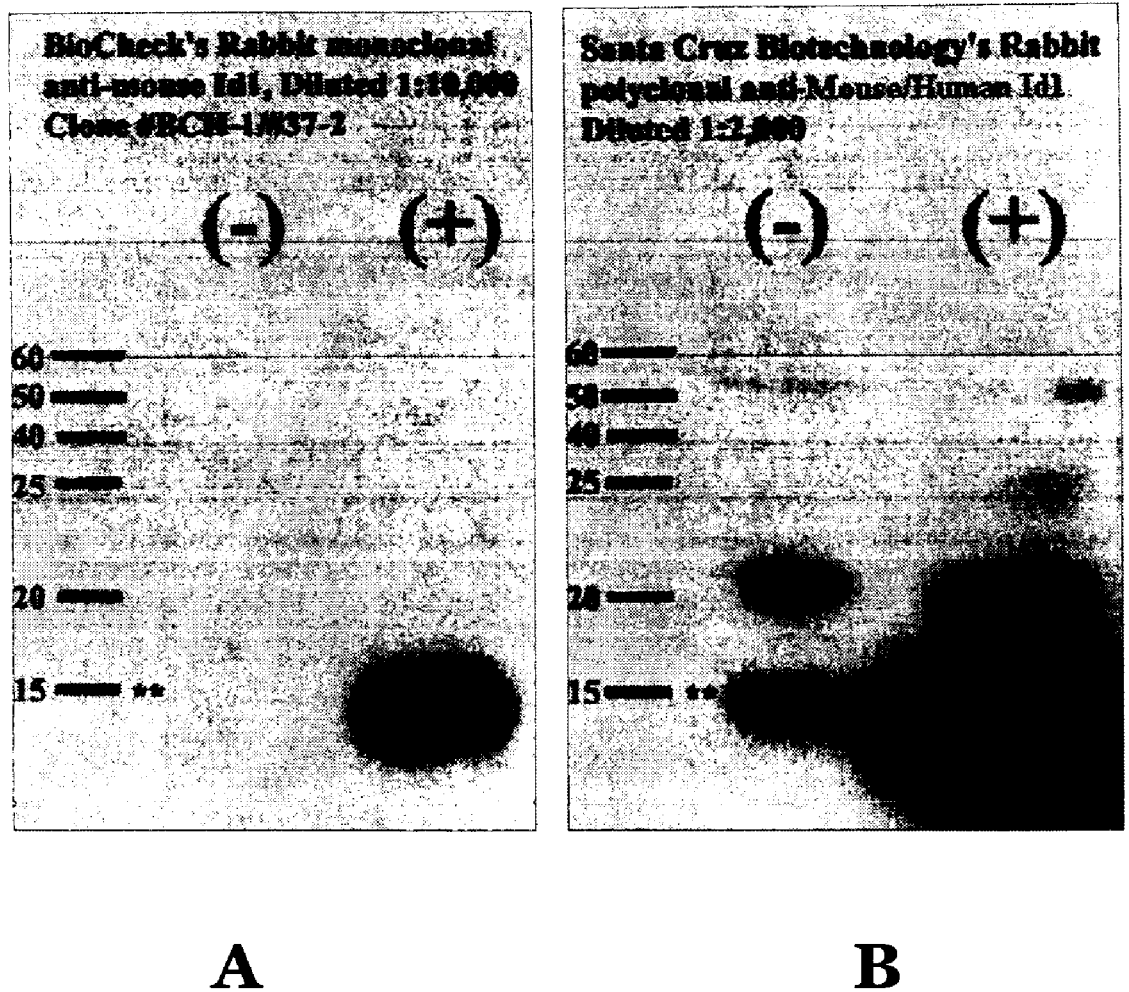
FIGS. 1A and 1B are a Western blot analyses of extracts from HeLa cells. Extracts in the (−) lanes are from untransfected cells that express human Id1. Extracts in the (+) lane are cells transfected to express both mouse Id1 and human Id1. The rabbit monoclonal anti-mouse Id1, clone #BCH-1/#37-2, of this invention was used to develop blot A. Santa Cruz Biotechnology's rabbit polyclonal anti-mouse/human Id1 was used to develop blot B. In these blots the molecular weight markers are kDa and the MW of Id1, ~15 kDa, is designated with **.

When present, unless otherwise specified, the following terms are generally defined as, but are not limited to, the following:

The term "antibody" refers to a specific protein binding partner for an antigen and is any substance, or group of substances, which has a specific binding affinity for an antigen to the exclusion of other substances. The generic term antibody includes polyclonal antibodies, monoclonal antibodies and antibody fragments (e.g. Fab' or (Fab')$_2$) of polyclonal antibodies or monoclonal antibodies. The generic term monoclonal antibodies include antibody fragments (e.g. Fab' or (Fab')$_2$) of monoclonal antibodies.

The term "affinity" refers to the strength with which an antibody molecule binds an epitope (antigenic determinant). Affinity can be quantified by determining an association constant.

The term "binding constant" or "equilibrium association constant" of an antibody refers to the value of [Ab–Ag]/[Ab][Ag] at equilibrium, where [Ab–Ag] is the concentration of antibody-antigen complexes, [Ab] is the unbound (free) concentration of antibody, and [Ag] is the unbound (free) concentration of antigen. The higher the binding constant, the higher the affinity of the antibody binds to the antigen. Equilibrium association constant is reciprocal of equilibrium dissociation constant.

The term "biological sample" refers to a sample from a living thing or formerly living thing. Such living things include, but are not limited to, human beings, mice, monkeys, rats, rabbits, horses, goats, and other animals. Such samples include, but are not limited to, blood, serum, plasma, urine, cells, organs, tissues, bone, bone marrow, lymph, lymph nodes, synovial tissue, chondrocytes, synovial macrophages, endothelial cells, and skin. Preferred biological samples for detecting Id1 are mouse or human tissue samples, or patient samples such as blood and plasma. The term also includes cell cultures derived from living things or formerly living things.

The term "conjugate" refers to any substance formed from the joining together of two parts.

The term "diagnostic" test, procedure, or instrument refers to a test, procedure, or instrument used to identify the nature or cause of an illness, disorder or problem.

The term "drug screening" refers to an assay used to determine the properties of a drug or drug candidate with respect to efficacy or safety or characteristics that impact on the safety or efficacy of a drug or drug candidate. These assays permit efficient prioritization and comparison of drugs or drug candidates The terms "immunogen" and "immunogenic" refer to substances capable of eliciting, producing, or generating an immune response in an organism.

The term "immunogenic carrier," refers to an immunogenic substance, commonly a protein, that can join with an antigen, in this case Id1, thereby enabling the Id1 to induce an immune response and elicit the production of antibodies that can bind specifically with the Id1. The immunogenic substances include proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Various protein types may be employed as immunogenic carriers. Illustrative proteins include bovine serum albumin (BSA), keyhole limpet hemocyanin (KLH), egg ovalbumin, bovine thyroglobulin (BTG), yellow fluorescent protein (YFP), or glutathione S-transferase (GST). Alternatively, synthetic polyamino acids may be utilized in place of proteins.

Immunogenic carriers can also include poly amino-polysaccharides, which are high molecular weight polymer built up by repeated condensations of monosaccharides. Examples of polysaccharides are starches, glycogen, cellulose, carbohydrate gums such as gum arabic, agar, and so forth. The polysaccharide may also contain polyamino acid residues and/or lipid residues. The immunogenic carrier can also be a polynucleic acids either alone or conjugated to one of the above mentioned polyamino acids or polysaccharides.

The term "label," or "a reporter molecule," refers to any molecule that produces, or can be induced to produce, a detectable signal. Non-limiting examples of reporter molecules include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor. Preferred reporter molecules are enzymes such as horseradish peroxidase, alkaline phosphatase, or β-galactosidase.

The term "prognostic" test refers to a test indicating likely course of an illness, disorder or problem.

The term "specificity" of an antibody refers to the antibody's ability to discriminate between two different epitopes.

The present invention is directed to rabbit monoclonal antibodies that bind to human Id1 protein and/or mouse Id1 protein. The rabbit monoclonal antibodies of the present invention are substantially specific for Id1 and do not substantially cross-react with other proteins such as other proteins of the Id family and other endogenous proteins. The antibodies are sufficiently sensitive in detecting and measuring Id1 at concentrations that are biologically significant in biological samples. The antibodies at the present invention are useful in immunoassays, Western blots, and immunohistochemistry.

The rabbit monoclonal antibodies of the present invention have a binding constant (equilibrium association constant), measured with respect to human Id1 protein or mouse Id1 protein, in general equal to or greater than $1 \times 10^7$ $M^{-1}$, preferably $1 \times 10^8$ $M^{-1}$, more preferably $1 \times 10^9$, more preferably $1 \times 10^{10}$, more preferably $1 \times 10^{11}$, more preferably $1 \times 10^{12}$, and most preferably $1 \times 10^{13}$. The high binding constant of the antibodies indicates high affinity of the antibodies to human Id1, and provides a high sensitivity for detection of Id1 protein.

The rabbit monoclonal antibodies of the present invention have no substantial cross-reactivity to other proteins of the Id family, e.g., Id2, Id3, and Id4 proteins, particularly Id2 and Id3; thus allows it to specifically detect the presence of Id1, instead of other Id proteins. The rabbit monoclonal antibodies of the present invention further have no substantial cross-reactivity to other endogenous proteins that are present in the cells that express Id1 protein. "No substantial cross-reactivity," as used herein, in general refers to <10%, preferably <5%, more preferably <2%, more preferably <1%, and most preferably <0.1%.

The specificity and high affinity of the rabbit monoclonal antibodies of the present invention allows sensitive and specific detection and quantitation of Id1 protein, thus providing a tool for sensitive and accurate diagnosis of a disease that results in the overproduction of Id1 such as breast cancer and other cancers. The antibodies are also useful in immunochemical-based assays to assess Id1 levels in various experimental biologic test systems, for example, systems that measure the ability of test chemicals to modulate Id1 protein concentration, Id1 protein activity, and Id1 gene expression.

Human Id1 protein and mouse Id1 protein have about 95% homology. The DNA sequence (SEQ ID NO:1) of human Id1 protein is as follows:

```
ATGAAAGTCG CCAGTGGCAG CACCGCCACC GCCGCCGCGG

GCCCCAGCTG CGCGCTGAAG GCCGGCAAGA CAGCGAGCGG

TGCGGGCGAG GTGGTGCGCT GTCTGTCTGA GCAGAGCGTG

GCCATCTCGC GCTGCGCCGG GGGCGCCGGG GCGCGCCTGC

CTGCCCTGCT GGACGAGCAG CAGGTAAACG TGCTGCTCTA

CGACATGAAC GGCTGTTACT CACGCCTCAA GGAGCTGGTG

CCCACCCTGC CCCAGAACCG CAAGGTGAGC AAGGTGGAGA
```

-continued

```
TTCTCCAGCA CGTCATCGAC TACATCAGGG ACCTTCAGTT

GGAGCTGAAC TCGGAATCCG AAGTTGGAAC CCCCGGGGGC

CGAGGGCTGC CGGTCCGGGC TCCGCTCAGC ACCCTCAACG

GCGAGATCAG CGCCCTGACG GCCGAGGCGG CATGCGTTCC

TGCGGACGAT CGCATCTTGT GTCGCTGA
```

The amino acid sequence (SEQ ID NO:2) for human Id1 protein is as follows:

```
MKVASGSTAT AAAGPSCALK AGKTASGAGE VVRCLSEQSV

AISRCAGGAG ARLPALLDEQ QVNVLLYDMN GCYSRLKELV

PTLPQNRKVS KVEILQHVID YIRDLQLELN SESEVGTPGG

RGLPVRAPLS TLNGEISALT AEAACVPADD RILCR
```

The DNA sequence for mouse Id1 (SEQ ID NO:3) protein is as follows:

```
ATGAAGGTCG CCAGTGGCAG TGCCGCAGCC GCTGCAGGCC

CTAGCTGTTC GCTGAAGGCG GGCAGGACAG CGGGCGAGGT

GGTACTTGGT CTGTCGGAGC AAAGCGTGGC CATCTCGCGC

TGCGCTGGGA CGCGCCTGCC CGCCTTGCTG GACGAGCAGC

AGGTGAACGT CCTGCTCTAC GACATGAACG GCTGCTACTC

ACGCCTCAAG GAGCTGGTGC CCACCCTGCC CCAGAACCGC

AAAGTGAGCA AGGTGGAGAT CCTGCAGCAT GTAATCGACT

ACATCAGGGA CCTGCAGCTG GAGCTGAACT CGGAGTCTGA

AGTCGGGACC ACCGGAGGCC GGGGACTGCC TGTCCGCGCC

CCGCTCAGCA CCCTGAACGG CGAGATCAGT GCCTTGGCGG

CCGAGGCGGC ATGTGTTCCA GCCGACGATC GCATCTTGTG

TCGCTGA
```

The amino acid sequence (SEQ ID NO:4) for mouse Id1 protein is as follows:

```
MKVASGSAAA AAGPSCSLKA GRTAGEVVLG LSEQSVAISR

CAGTRLPALL DEQQVNVLLY DMNGCYSRLK ELVPTLPQNR

KVSKVEILQH VIDYIRDLQL ELNSESEVGT TGGRGLPVRA

PLSTLNGEIS ALAAEAACVP ADDRILCR
```

In one embodiment of the invention, the rabbit monoclonal antibodies (anti-human Id1 antibodies) only have reactivity toward human Id1 protein and have no substantial reactivity toward mouse Id1 protein; i.e., the antibodies have a ratio of binding constant toward human Id1 protein and mouse Id1 protein of greater than 10:1, preferably 20:1, more preferably 40:1, and most preferably 100:1.

In one embodiment of the invention, the rabbit monoclonal antibodies (anti-mouse Id1 antibodies) only have reactivity toward mouse Id1 protein and have no substantial reactivity toward human Id1 protein; i.e., the antibodies have a ratio of binding constant toward mouse Id1 protein and human Id1 protein of greater than 10:1, preferably 20:1, more preferably 40:1, and most preferably 100:1.

In further embodiment of the invention, the rabbit monoclonal antibodies (anti-human/mouse Id1 antibodies) have substantial reactivity toward both human Id1 and mouse Id1 protein; i.e., the antibodies have a ratio of binding constant toward human Id1 protein and mouse Id1 protein of between 1:2 to 2:1. These antibodies have binding constants, measured with respect to mouse Id1 protein and human Id1 protein, in general equal to or greater than $1\times10^8$ $M^{-1}$, preferably $1\times10^9$, more preferably $1\times10^{10}$, more preferably $1\times10^{11}$, more preferably $1\times10^{12}$, and most preferably $1\times10^{13}$. These antibodies are useful to measure Id1 in test systems that combine cells and other materials from both human and murine sources. One example of this type of application is the measurement of Id1 in samples from immuno-compromised mice inoculated with human cancer cells, a common model of human cancer used extensively in efforts to discover agents to treat cancer (Dykes et al., Contrib. Oncolo. Basel, Karger, 1992, Vol 42, pp 1-22).

The rabbit monoclonal antibodies of this invention are obtained from rabbit hybridomas. These are formed by the fusion of rabbit plasmacytoma cells and B lymphocytes from the spleen cells of rabbits immunized against Id1 conjugates. These rabbit hybridomas that secrete Id1 monoclonal antibodies are produced by the procedure of Knight [Spieker-Polet et al., Proceeding National Academy Science USA; 92: 9348-9352 (1995) and U.S. Pat. No. 5,675,063]. B lymphocytes are taken from the immunized rabbit spleen cells which have been transformed so that they express at least two oncogenes, preferably two oncogenes such as myc and abl. These cells are the fusion partner, i.e., plasmacytomas, for hybridoma production of the anti-Id1 polyclonal cells isolated from the immunized rabbits.

An immunogen of human Id1 is prepared for immunization of rabbits for producing the monoclonal antibody. The immunogen is an immunogenic conjugate of a human Id1 protein and an immunogenic protein formed by any conventional manner. The immunogenic conjugate is preferably prepared as a fusion protein of Id1 with an immunogenic protein having a reactive functional group, particularly a carboxylic acid group, or cloned in frame with the protein of interest. This cloning procedure results in the fusion protein. The immunogenic protein also allows the immunogen to be immobilized either on a purification column or on a solid carrier medium. Any of the commonly used immunogenic proteins such as bovine serum albumin (BSA), keyhole limpet hemocyanin (KLH), egg ovalbumin, bovine thyroglobulin (BTG), yellow fluorescent protein (YFP), or glutathione S-transferase (GST), can be used for this invention. Alternatively, synthetic polyamino acids can be used in place of proteins. Preferred immunogenic proteins are His-tag (His), yellow fluorescent protein (YFP), and glutathione S-transferase (GST). The His, GST or YFP can be cloned at the N-terminal (amino terminal) or the C-terminal (carboxyl terminal) of Id1. The fusion protein can be produced by conventional recombinant techniques for producing fusion proteins. In this method, the plasmid is prepared containing the DNA of human Id1 and the DNA for the immunogenic protein. The plasmid can then be inserted into E. coli cells, which then express the fusion protein of Id1-immunogenic protein conjugate. The fusion protein can be purified by utilizing any conventional affinity column and thereafter eluted from the column in a pure form by conventional means. The purified fusion proteins prepared in this manner are used as the immunogen to produce the antibodies.

Rabbits are immununized with the immunogen (human Id1-immunogenic protein conjugate). Rabbits with high titer against human Id1 protein are selected. B lymphocytes are taken from the selected rabbit and fused with plasmacytoma cell lines developed from transgenic rabbits carrying at least two transgenes, preferably two oncogenes such as myc and abl.

In preparing the rabbit hybridomas, B lymphocytes obtained from the spleen, peripheral blood, lymph nodes or other tissue of the immunized rabbits can be used as the monoclonal antibody producing cells; B lymphocytes obtained from the spleen are preferred. Hybridomas are obtained by fusing such B lymphocytes with an immortal cell line, which is a cell line that imparts long term tissue culture stability on the hybrid cell. In a preferred embodiment of the invention, the immortal cell is a lymphoblastoid cell or a plasmacytoma cell such as a myeloma cell, which is an antibody producing cell and is malignant. Supernatants of the hybridomas are screened to select the optimal hybridomas that have desirable Id1 binding properties. The selected hybridomas are cloned and cryopreserved.

In accordance with this invention, the rabbit monoclonal anti-mouse Id1, rabbit monoclonal anti-human Id1, and rabbit monoclonal anti-mouse/human Id1 are developed by immunizing rabbits with mouse or human Id1 protein conjugated to an immunogenic protein such as GST or KLH. Hybridoma clones secreting Id1 antibody were selected through ELISA screen of hybridoma supernatants. Further screen of the ELISA positive clones are performed by Western Blot and immunohistochemistry to identify hybridoma clones suitable for these two applications.

The antibodies produced are tested against various antigens to determine their cross-reactivity, particularly the Id2, Id3, and Id4 members of the Id family of proteins. Table 1 shows the reactivity of one type of antibody (anti-human Id1) of the present invention toward various proteins.

TABLE 1

Reactivity of anti-human Id1 antibodies toward proteins

| Protein | Binding Constant (%) |
| --- | --- |
| Human Id1 | 100 |
| Mouse Id1 | <5 |
| Human Id2, Mouse Id2 | <1 |
| Human Id3, Mouse Id3 | <1 |
| Human Id4, Mouse Id4 | <1 |

Table 2 shows the reactivity of a second type of antibody (anti-mouse Id1) of the present invention toward various proteins.

TABLE 2

Reactivity of anti-mouse Id1 antibodies toward proteins

| Protein | Binding Constant (%) |
| --- | --- |
| Human Id1 | <5 |
| Mouse Id1 | 100 |
| Human Id2, Mouse Id2 | <1 |
| Human Id3, Mouse Id3 | <1 |
| Human Id4, Mouse Id4 | <1 |

Table 3 shows the reactivity of a third type of antibody (anti-human Id3/anti-mouse Id3) of the present invention toward various proteins.

TABLE 3

Reactivity of anti-human Id1/anti-mouse Id1 antibodies toward proteins.

| Protein | Binding Constant (%) |
| --- | --- |
| Human Id1 | 100 |
| Mouse Id1 | 50–200 |
| Human Id2, Mouse Id2 | <1 |
| Human Id3, Mouse Id3 | <1 |
| Human Id4, Mouse Id4 | <1 |

Chimeric and humanized monoclonal antibodies can be produced by cloning the antibody expressing genes from the hybridoma cells and employing recombinant DNA methods well known in the art to either join the subsequence of the rabbit IgG variable region to human IgG constant regions or to combine human framework regions with complementary determining regions (CDRs) from a donor rabbit immunoglobulin. An improved method for carrying out humanization of rabbit monoclonal antibodies, which provides antibodies of enhanced affinities is set forth in International Patent Application WO 92/11018.

Polypeptide fragments of the monoclonal antibodies comprising only a portion of the primary antibody structure can be prepared. These polypeptide fragments, which can maintain the activity of the parent monoclonal or even provide improved characteristics, can be produced by proteolytic cleavage of intact antibodies by methods well known in the art, or by inserting stop codons at the desired locations in expression vectors containing the antibody genes using site-directed mutagenesis to produce Fab fragments or (Fab)$_2$ fragments. Single chain antibodies can be produced by joining VL and VH regions with a DNA linker [see Huston et al., Proc. Natl. Acad. Sci. U.S.A., 85:5879-5883 (1988) and Bird et al., Science, 242:423-426 (1988)].

The rabbit-monoclonal antibodies of the present invention are useful for preparing reporter molecule-antibody conjugate.

Antibodies having reactivity toward human Id1 protein and/or mouse Id1 protein are useful in immunoassays for detecting and/or quantifying Id1 protein of a given species in biological samples, particularly for diagnostic, prognostic, drug monitoring, or research purpose.

The present invention is directed to a method of determining the concentration of human Id1 or mouse Id1 in a liquid sample. The method comprises the steps of: (a) reacting a liquid sample with an antibody, which binds to human Id1 or mouse Id1 and has no substantial cross-reactivity with human or mouse Id2, Id3, or Id4; (b) forming an immunocomplex between Id1 in the sample and the antibody, and (c) determining the amount of immunocomplex formed. The antibody can be any polyclonal or monoclonal antibody, or its fragment that has high affinity toward human Id1 or mouse Id1, i.e. having a binding constant equal to or greater than $1\times10^8$ M$^{-1}$, preferably $1\times10^9$, more preferably $1\times10^{10}$, more preferably $1\times10^{11}$, more preferably $1\times10^{12}$, and most preferably $1\times10^{13}$. The immunoassay is sensitive to detect 0.5 ng/mL of less of Id1 in a sample at 100 μL sample volume.

Immunoassays include sandwich assays and competitive assays (see Sittampalm, et al. (1996) J. Immunol. Methods, 190:151-161; Vann, et al.(1990) Methods Enzymol. 184:537-541). A sandwich assay is used to determine the concentration of an antigen in a sample. A first antibody is attached to a solid support. When a solution containing an antigen of interest is added to the well, the bound antibody captures the antigen, and any unbound antigen is removed by washing. A second antibody, which recognizes a separate epitope from that of the first antibody, binds to the antigen that is already bound to the solid phase via the primary antibody. Excess secondary antibody is removed by washing. The secondary antibody is often labeled by a reporter molecule to facilitate detection or quantitation.

In a competitive assay, an antigen is bound to a solid support. Unbound antigen is removed by washing and any other protein binding sites on the solid support are tied up by incubation with a blocking reagent (often a nonfat dry milk solution). The solid support is then incubated with known amounts of antigen, sample solution, and antibody-reporter molecule conjugate. The amount of antibody-reporter molecule conjugate that binds to the solid support is inversely proportional to the amount of antigen contained in the sample.

In one embodiment, the present invention is directed to a sandwich assay for determining the concentration of human Id1 or mouse Id1 in a liquid sample. The assay comprises the steps of: (a) reacting a liquid sample with a first antibody attached on a solid support and a second antibody in the liquid phase, wherein the first antibody and the second antibody bind to human Id1 or mouse Id1 at different epitopes and have no substantial cross-reactivity against human or mouse Id2, Id3, or Id4; (b) forming an immunocomplex among Id1 in the sample, the first antibody, and the second antibody; and (c) determining the amount of immunocomplex formed. In one aspect, the Id1 in the liquid sample contacts the first antibody before contacting the second antibody. In another aspect, the liquid sample contacts the first antibody and the second antibody simultaneously. The immunocomplex is preferably determined by detecting the reporter molecule conjugated to the second antibody. The first antibody and the second antibody can be any polyclonal or monoclonal antibody, or its fragment that has high affinity toward human Id1 or mouse Id1 i.e. having a binding constant equal to or greater than $1\times10^8$ $M^{-1}$, preferably $1\times10^9$, more preferably $1\times10^{10}$, more preferably $1\times10^{11}$, more preferably $1\times10^{12}$, and most preferably $1\times10^{13}$. Preferably, the second antibody is a rabbit monoclonal antibody and labeled with a reporter molecule.

In another embodiment, the present invention is directed to a competitive assay for determining the concentration of human Id1 or mouse Id1 in a liquid sample. The assay comprises the steps of: (a) contacting the sample with a solid-phase support having surface-attached human Id1 or mouse Id1 molecules in the presence of an antibody labeled with a reporter molecule, wherein said surface-attached Id1 is effective to compete with Id1 in the sample for binding to the antibody, (b) forming an immunocomplex between Id1 in the sample and the antibody, and (c) determining the amount of immunocomplex formed. The antibody can be either a polyclonal antibody, or monoclonal antibody, or its fragment that binds to human Id1 or mouse Id1 with a binding constant equal to or greater than $1\times10^8$ $M^{-1}$, preferably $1\times10^9$, more preferably $1\times10^{10}$, more preferably $1\times10^{11}$, more preferably $1\times10^{12}$, and most preferably $1\times10^{13}$; with no substantial cross-reactivity with human Id3, Id2, or Id4. Preferably, the antibody is a rabbit monoclonal antibody and labeled with a reporter molecule.

Any suitable solid support commonly used for immunoassays including, but not limited to polystyrene, nitrocellulose, nylon, latex, can be used for the present invention. Microtiter plates (polystyrene) are an example of the solid support of the present invention.

Antibodies of the present invention are useful in a method for detecting human Id1 or mouse Id1 in a tissue sample, e.g. western blot and immunohistochemistry staining (IHC staining). The antibody is a rabbit monoclonal antibody, or its fragment that binds to human Id1 or mouse Id1 with a binding constant equal to or greater than $1\times10^8$ $M^{-1}$, preferably $1\times10^9$, more preferably $1\times10^{10}$, more preferably $1\times10^{11}$, more preferably $1\times10^{12}$, and most preferably $1\times10^{13}$; with no substantial cross-reactivity with human Id2, Id3, or Id4.

The western blot method comprises the steps of (a) obtaining a sample of tissue homogenate or tissue extract; (b) applying the sample on gel; (c) performing gel electrophoresis and separating proteins in the sample by molecular weight; (d) transferring the proteins out of the gel and onto a membrane; (e) reacting the membrane with an antibody that binds to human Id1 or mouse Id1, which forms an immunocomplex with Id1 in the sample; and (f) detecting the immunocomplex.

The IHC staining method comprises the steps of (a) reacting a tissue sample with an antibody that binds to human Id1 or mouse Id1, (b) forming an immunocomplex between Id1 in the tissue sample and the antibody, and (c) detecting the immunocomplex formed by staining.

The immunocomplex in the western blot and IHC staining can be detected by two different approaches, as well known by a skilled person. The antibody can be conjugated to a reporter molecule and the reporter molecule is detected. Alternatively, a secondary antibody (e.g. anti-rabbit IgG or anti-mouse IgG) that is conjugated to a reporter molecule is added to the immunocomplex and binds to the immunocomplex, and the reporter molecule is detected.

The rabbit monoclonal antibody of the present invention can be used for research purpose or for diagnostic purpose. For diagnostic purpose, the method comprises the exposure of a liquid sample or a solid sample known or suspected to contain Id1 to a diagnostic device that includes a diagnostic reagent comprising the rabbit monoclonal antibody under conditions that allow the Id1, if present, to bind to the diagnostic reagent, which can be derivatized for detection before, or after, binding of Id1.

The rabbit monoclonal antibody of the present invention can be used for prognostic test. For prognostic test, the method comprises the exposure of a liquid sample or a solid sample known or suspected to contain Id1 to a prognostic device that includes a prognostic reagent comprising the rabbit monoclonal antibody under conditions that allow the Id1, if present, to bind to the prognostic reagent, which can be derivatized for detection before, or after, binding of Id1.

The rabbit monoclonal antibody of the present invention can be used for drug screening assay. For drug screening assay, the method comprises the exposure of a liquid sample or a solid sample known or suspected to contain Id1 to a drug screening device that includes a drug screening reagent comprising the rabbit monoclonal antibody under conditions that allow the Id1, if present, to bind to the drug screening reagent, which can be derivatized for detection before, or after, binding of Id1.

The following examples further illustrate the present invention. These examples are intended merely to be illustrative of the present invention and are not to be construed as being limiting.

EXAMPLES

Example 1

Preparation of Mouse Antigen: Transformation of *E. coli* Cells for Production of Cloned Mouse Id1

*E coli* cells were transformed to produce cells capable of providing useful quantities of modified mouse Id1 proteins suitable for use as antigens. In one embodiment, the full length coding region gene for mouse Id1 (GenBank Accession No. NM-010495, 68-514 base pairs) was cloned into a pGEX-4T-3 vector (Amersham BioScience, GenBank Accession No. U13855). The pGEX vector allows for cloning the gene of interest, in this case mouse Id1, in frame with the glutathione S-transferase (GST). pGEX was treated with the appropriate restriction enzyme (EcoRI) for insertion of mouse Id1 gene. The resulting mId1-GST vector was used to transform BL21 strain of E. coli (Stratagene). Following Stratagene's transformation protocol, the E. coli competent cells were thawed on ice. After thawing, the cells were gently mixed and 100 µL aliquots of cells were transferred into 14-ml polypropylene round bottom tubes (BD Falcon). 1.7 µL of 1:10 diluted 12.5 M β-mercaptoethanol (β-ME) was added to each tube containing the competent cells to give a final β-ME concentration of 25 mM. The tubes were gently mixed and incubated on ice for 10 minutes with gentle swirling every 2 minutes. 1-50 ng of the mId1-GST vector was added to each transformation reaction and gently mixed. The reaction mixture was incubated on ice for 30 minutes. The transformation reaction mixture was heat-pulsed for 45 seconds in a 42° C. water bath. The incubation reaction was placed on ice for 2 minutes. 0.9 mL of preheated (42° C.) SOC medium was added to each transformation reaction and incubated at 37° C. for 1 hour with shaking at 225-250 rpm. Using a sterile spreader, ~200 mL of the transformed cells were spread onto LB-agar plates containing ampicillin. The plates were incubated overnight at 37° C. Colonies grown overnight were transformed BL21 cells with the pGEX-4T-mId1 plasmid, and the cells transferred and grown in LB media containing appropriate antibiotics (ampicillin) to log phase. The BL21 cells were then aliquoted into 1.5 mL microcentrifuge tube. Glycerol was added to a final concentration of 14% and the cells stored at −80° C. for future use.

Example 2

Preparation of Mouse Antigen and Immunogen: Production and Purification of Mouse Id1:GST from Transformed E. coli Mouse Id1 proteins useful as antigens were produced from cells of Example 1. In one embodiment for protein preparation, the auto-induction system (Novagen) in LB media was inoculated with BL21 with pGEX-4T-mId1 plasmid. The BL21 cells were grown in this system at 30° C. with shaking at 225 rpm. The BL21 cell growth was monitored by checking the optical density of the media at intervals of every 6 hours until the cells were grown to an optical density of 3. The media was then centrifuged at 5000 rpm to pellet the cells. The supernatant was discarded and the pelleted cells were lysed using B-PER lysis reagent (Pierce, Inc.). Following the manufacturer's purification protocol, the Immobilized Glutathione Column was equilibrated with 10 mL of B-PER reagent (Pierce). 10 mL (2×5 mL) of cell lysate was applied to the column and allowed the sample to flow completely through the gel bed. The column was washed with 3 mL of Wash Buffer 1 (Pierce), and can be repeated up to three times. The column was washed with Wash Buffer 2 (Pierce). The elution buffer was prepared using 12 mL of Wash Buffer 2 to one vial containing 184 mg GST. The fusion protein was eluted four times with 3 mL of elution buffer. Each 3 mL fraction was collected and absorbance was measured at 280 nm to monitor the elution of mId1:GST from the column. The protein concentration of mId1:GST was determined. Purity of mId1:GST was checked using sodium dodecyl sulphate-polyacrylamide gel electrophoresis (SDS-PAGE).

Example 3

Preparation of Human Antigen: Transformation of E. coli Cells for Production of Cloned Human Id1

E. coli cells were transformed to produce cells capable of providing useful quantities of modified human Id1 proteins suitable for use as antigens. In one embodiment, cells capable of producing human Id1 proteins useful as antigen were prepared by means of the procedure given in Example 1 except the plasmid pGEX-4T-3 vector with h-Id1 (human Id1) instead of m-Id1 (mouse Id1) was used, i.e., the DNA inserted was human Id1 instead of the mouse Id1 DNA to produce the transformed E. coli cells for expressing human Id1 protein and the human Id1 is in frame with six (6) Histidine residues (His-tag) instead of GST.

Example 4

Preparation of Human Antigen: Production and Purification of Human Id1:His from Transformed E. coli Human Id1 proteins useful as antigens were produced from cells of Example 3. Human Id1:His was prepared from E. coli cells of Example 3 which are transformed to express human Id1 by the procedure given in Example 2.

Example 5

Preparation, Production and Purification of Miscellaneous Proteins Used in Antibody Production, Screening and Characterization Various additional Id1-related proteins were produced to use for antibody screening and characterization using the appropriate Id1 DNA in place of the DNA for mouse Id1. In this manner, the fusion proteins listed in Table 4 were also produced by the procedures of Examples 1 and 2.

TABLE 4

Vectors Used to Make Miscellaneous Proteins Supporting Production Rabbit Antibodies to Mouse Id1 and Human Id1

| Protein | Vector |
|---|---|
| Mouse Id1:Histidine | Gene for m-Id1-His litigated into pGW07 |
| Mouse Id1:yellow fluorescent protein | Gene for m-Id1 litigated into pEYFP and result ligated into pAL |
| Human Id1:Histidine | Gene for h-Id1:his litigated into pGW07 |
| Mouse Id2:Histidine | Gene for m-Id2:His litigated into pGW07 |
| Human Id2:Histidine | Gene for h-Id2:His litigated into pGW07 |
| Mouse Id3:Histidine | Gene for m-Id3:His litigated into pGW07 |
| Human Id3:Histidine | Gene for h-Id3:His litigated into pGW07 |
| Mouse Id4:Histidine | Gene for m-Id4:His litigated into pGW07 |
| Human Id4:Histidine | Gene for h-Id4:His litigated into pGW07 |

Example 6

Preparation of Human Immunogens

Human Id1 Immunogens were prepared by means of the procedure given in Examples 3 and 4 except the human Id1 is in frame with the protein immunogen KLH.

Example 7

Procedure for Producing Rabbit Polyclonal Anti-Mouse Id1

Preparation of Id1 Coupled Affinity Column

Procedure used for coupling Id Proteins to CNBr-Activated Sepharose 4 Fast Flow is summarized below:
1. Suspend the pre-activated gel in 1 mM HCl for 30 minutes and allow to swell.
2. Wash with 15 gel volumes of cold 1 mM HCl.
3. Wash with coupling buffer (0.1 M NaHCO$_3$, 0.5 M NaCl, pH 8.3).
4. Dissolve the Id protein in coupling buffer and adjust to pH 8.3.
5. Add the washed gel to the Id protein solution and incubate overnight at 4° C. or at room temperature for 3-4 hours).
6. Wash and resuspend the coupled gel in 1 M ethanolamine for 2-4 hours at room temperature to block unused activated sites.
7. Wash the gel 8 times with alternating 50 mM Tris, 1 M NaCl, pH 8.0 and 50 mM glycine, 1 M NaCl, pH 3.5 buffers.
8. Wash the gel with 10 gel volumes of PBS.

Preparation of Affinity Purified Rabbit Polyclonal Antiserum

Rabbits were immunized as follows to produce antisera to the mouse Id1:GST. Each rabbit was initially intradermally injected to ten (10) sites with mouse Id1:GST prepared in Examples 1 and 2 at 1.0 mg/mL with complete adjuvant. Subsequent boost injections were injected intradermally to ten (10) sites with Id1:GST at 0.3 mg/mL with incomplete adjuvant on days 20, 34, 48, 77, 108 and 137 since initial injection. The immune-response of each rabbit was monitored via ELISA as set forth in Example 9 with mouse Id1:his and GST coated micro titer wells. The rabbit antisera were diluted 1:8000 in 0.01 5M KPO4 buffer, pH 7.4 containing 0.25% (w/v) BSA, 0.85% (w/v) NaCl, and 0.1% (w/v) NaN$_3$ for the ELISA tests. The rabbit with the highest anti-mouse Id1 antibody titer of the three rabbits was sacrificed on Day 115 after the initial injection. The antiserum obtained from this rabbit prior to sacrifice was purified via an Id1 antigen-affinity column to obtain affinity purified rabbit polyclonal anti-mouse Id1.

Example 8

Procedure for Producing Rabbit Polyclonal Anti-Human Id1

By the procedure of Example 7, rabbits were immunized using human Id1:KLH fusion protein prepared in Example 6.

The rabbit with the highest anti-human Id1 antibody titer of the three rabbits was sacrificed on Day 122 after the initial injection. The antiserum obtained from this rabbit prior to sacrifice was purified via an Id1 antigen-affinity column to obtain affinity purified rabbit polyclonal anti-human Id1.

Example 9

Method for Screening Polyclonal Antibody Titer

The method described below was used to determine rabbits that had a polyclonal antibody titer suitable for subsequent monoclonal antibody production.

Materials
1. The microtiter wells used for assays to determine antibody production and reactivity were coated (0.1 µg/well) with the following antigens previously prepared: mouse Id1:YFP, mouse Id1:GST, mouse Id1:His, human Id1:His, mouse Id2:His, human Id2:His, mouse Id3:His, human Id3:His, GST, and X (which can be any conventional protein partner for the immunogen, e.g. KLH).
2. Antibody diluent: 0.25% (w/v) BSA in 0.015M KPO4 Buffer, 0.85% (w/v) NaCl, 0.1% (w/v) NaN$_3$, pH=7.40
3. Sera from rabbits immunized with mouse Id1:GST as described in Example 7 diluted 1:8,000 in antibody diluent, or sera from rabbits immunized with human Id1:X as described in Example 8 diluted 1:8,000 in antibody diluent.
4. Goat anti-rabbit IgG HRP conjugate diluted 1:50K with conjugate diluent, i.e., 50% (v/v) fetal Bovine Serum in 0.05 M Tris, 1% (v/v) Proclin-300, pH 7.6
5. TMB Reagent
6. Stop Solution (1 N HCl)

Procedure for Antigen Coated Plates

The buffers for plate coating were as follows: 0.2 M sodium phosphate (NaPO$_4$) pH 6.5 buffer, 10 mM potassium phosphate (KPO$_4$) pH 7.4 buffer, 1% (w/v) BSA in 10 mM potassium phosphate (KPO$_4$), pH 7.4 buffer with 0.1% (w/v) sodium azide (NaN$_3$), and 2.5% (w/v) sucrose in 10 mM potassium phosphate (KPO$_4$), pH 7.4 buffer. The plates were coated with the above antigens by the following procedure:
1. Prepare antigen solution by mixing 0.2 M NaPO$_4$ with antigen for the appropriate coating concentration.
2. Stir solution at room temperature for 10 minutes.
3. Saturate pipet delivery system for 10 minutes.
4. Dispense 100 µL of antigen solution into each well.
5. Incubate plates at 2-8° C. overnight (16-24 hours).
6. Shake off the antigen solution.
7. Wash each well with 300 µL of 10 mM KPO$_4$ buffer.
8. Shake off the KPO4 buffer.
9. Dispense 150 µL of 1% BSA solution into each well.
10. Incubate plates at 2-8° C. overnight (16-24 hours).
11. Shake off the BSA solution.
12. Dispense 250 µL of 2.5% sucrose solution into each well.
13. Incubate plates at 2-8° C. for 4 hours.
14. Shake off sucrose solution.
15. Dry in vacuum at room temperature overnight.

Screening Method
1. Dispense 100 µL of antibody diluent, diluted rabbit polyclonal anti-Id1 into appropriate wells.
2. Incubate at room temperature with mechanical shaking at 750 rpm for 90 minutes.
3. Remove the incubation mixture by flicking plate content into an appropriate waste container, followed by rinsing the wells 5 times with distilled water.
4. Strike the wells sharply onto absorbent paper or paper towels to remove all residual water droplets.
5. Dispense 100 µL of Goat Anti-Rabbit IgG-HRP Conjugate Reagent into each well. Gently mix for 5 seconds.
6. Incubate at room temperature with mechanical shaking at 750 rpm for 90 minutes.
7. Repeat procedures 3 and 4.
8. Dispense 100 µL of TMB Reagent into each well. Gently mix for 5 seconds.
9. Incubate at room temperature with mechanical shaking at 750 rpm for 20 minutes.
10. Add 100 µL of Stop Solution (1N HCl) into each well.
11. Gently mix for 10 seconds to ensure a complete mixing.
12. Read optical density (absorbance) at 450 nm.

Results from this assay were used to select the rabbit sera with the highest antibodies titer that selectively reacts with mouse Id1 or human Id1 or both.

Example 10

Preparation of Rabbit Monoclonal Anti-Mouse Id1

Transgenic rabbits were created to provide plasmacytoma cells suitable for hybridoma formation with splenocytes from animals with suitable antibody titer.

(a) Transgenic Rabbits

Single-cell zygotes were injected with a murine $E_\mu$-abl construct at a concentration of 1 µg/ml and implanted into the uterus of pseudopregnant females. Offspring were tested at 3-4 weeks of age by Southern blot analysis of peripheral blood lymphocyte DNA for the presence of the $E_\mu$-abl transgene. Rabbits carrying the $E_\mu$-abl transgene were mated with $E_K$-myc transgenic rabbits. The offspring were tested for the presence of both transgenes as described above. In addition, zygotes from a transgenic $E_K$-myc rabbit with the $E_\mu$-abl transgene were microinjected directly.

(b) Generation of Plasmacytoma Cell Lines and Hypoxanthine/Aminopterin/Thmidine (HAT)-Sensitive Fusion Partner Rabbits that became ill were sacrificed and cells from the tumorous tissues were placed in tissue culture in an attempt to obtain plasmacytoma cell lines. Culture medium used was RPMI 1640 enriched with the following additions: amino acids, nonessential amino acids, pyruvate, glutamine, vitamins, Hepes, gentamicin, penicillin, streptomycin, fungizone (all components were from GIBCO and were used at concentrations suggested by the supplier), and 50 µM β-mercaptoethanol. After 6-8 weeks in culture, stable cell lines were growing from these tumorous tissues.

To obtain a HAT-sensitive fusion partner, three cell lines were first X-irradiated with 200 rad (1 rad=0.01 Gy) and then cultured in the presence of 8-azaguanine. (The concentration of 8-azaguanine was initially 0.2 µg/ml and was slowly increased to 20 µg/ml over a 10-month period). Three 8-azaguanine-resistant clones were obtained after one month and two after 8 months in culture. Cells of these clones were sensitive to medium containing HAT.

(c) Isolation of Splenocytes for Rabbit Monoclonal Anti-mouse Id1

Id1—Spleen cells from rabbit sacrificed in Example 7 were harvested and isolated by crushing the spleen in RPMI 1640 medium and filtering through 100-µm strainers, followed by treatment with red cell lysis buffer (Sigma). The isolated splenocytes were kept in 10% dimethyl sulfoxide and 90% FBS at −80° C. until use.

(d) Hybridoma Development for Rabbit Monoclonal Anti-mouse Id1

To generate the rabbit monoclonal anti-mouse Id1 hybridoma, the splenocytes were fused with the rabbit plasmacytoma cell line in part (b) at a ratio of 2:1 with 50% (w/v) polyethylene glycol (Sigma). Two fusions were performed. The fused cells were plated at a density of $5 \times 10^5$ cells/well in 96-well plates in RPMI 1640 supplemented with 10% fetal bovine serum (FBS), amino acids, vitamins, HEPES, sodium pyruvate, β-mercaptoethanol and antibiotics (gentamicin/penicillin/streptomycin/fungizone). After 24 hour incubation, hypoxanthine, aminopterin, and thymidine (HAT) containing medium was added and FBS was brought up to 15%. Medium in fusion plates was changed after four weeks.

(e) Positive Clone Identification for Rabbit Monoclonal Anti-Mouse Id1

Seven days after medium change, positive rabbit monoclonal anti-mouse Id1 hybridomas were identified via ELISA, using plates pre-coated with mouse Id1:His as described in Example 9. Positive hybridoma clones were transferred and expanded into 24-well plates. The expanded hybridoma supernatants were further screened for rabbit monoclonal anti-mouse Id1 positive clones by ELISA using plates pre-coated with mouse Id1:His or GST as described in Example 9. The supernatants from hybridoma clones showing positive on mouse Id1:His plates but negative on GST plates were collected for serial dilution ELISA performed to select strong positive clones without cross-reactivity to GST. Such clones were identified. To ensure for monoclonal hybridoma, the clones were subcloned with limiting dilution. Subclones with high ELISA titers were selected for large quantity antibody production.

(f) Monoclonal Antibody Production

Concentrated antibody production was conducted in an Integra flask. A subclone of the identified clone, was expanded to two T175 flasks in RPMI medium with 10% FBS, 1× HAT and other supplements. Prior to inoculation into an Integra flask, the cells were adapted to a low serum medium (25% RPMI with 10% FBS and 75% BD niAb serum-free medium) overnight. About $2 \times 10^7$ cells were inoculated and grown in BD mAb serum free medium. The medium in nutrient compartment of the flask was changed ten days after inoculation. After another ten days, supernatant in the cell compartment of the flask was harvested.

Example 11

Preparation of Rabbit Monoclonal Anti-Human Id1

By the same procedure of Example 10, the spleen cells of the rabbit sacrificed on day 122 in Example 8 was used to produce rabbit monoclonal anti-human Id1.

Example 12

Sequences of Selected Rabbit Monoclonal Antibodies and Recombinant Expression of Id1 Antibodies Positive rabbit clones secreting monoclonal antibodies against mouse Id1 and/or human Id1 were selected utilizing the procedures described in Example 9, except rabbit monoclonal anti-mouse Id1 from supernatants of the hybridomas produced in Example 10 and rabbit monoclonal anti-human Id1 supernatants of the hybridomas produced in Example 11 were used instead of rabbit polyclonal antisera. All supernatants were diluted 1:10 in antibody diluent prior to analysis.

Total RNAs were isolated from hybridomas of Clone #BCH-1/#37-2, #BCH-1/#195-14, and #BCH-2/#5-3, using Qiagen RNaesy Mini Kit (Catalog #74104). cDNAs were made from the total RNA by Oligo dT directed reverse transcription (reverse transcriptase, Promega Improm II, from Promega, Catalog #M314A).

Rabbit IgG cDNA were amplified with heavy or light chain specific primers (designed by Epitomics, Inc., Burlingame, Calif., and synthesized by Elim Biopharmaceuticals, Inc., Hayward, Calif.) by PCR (DNA polymerase, TaqPlus Precision, purchased from Stratagene Corp, La Jolla, Calif., Catalog #600211-51). The IgG heavy and light chain sequences of the selected clone were obtained by sequencing the PCR products (sequencing services provided by Elim Biopharmaceuticals, Inc.). For recombinant expression of anti-Id1 antibody, the PCR product was cloned into pcDNA3 or pTT5 vector. Recombinant Id1 antibody was transiently expressed in HEK 293 cells with plasmid DAN transfection.

The selected rabbit monoclonal anti-mouse Id1, clone #BCH-1/#37-2, had the following DNA and amino acid sequence:

```
Variable Light Chain Sequence
(Nucleotide/Peptide, SEQ ID NO: 5/6), 336 nt
CGAGTGCTGACCCAGACTGCATCCCCCGTGTCTGCGGCTGTTGGAGGCACAGTCACCATC
  R   V   L   T   Q   T   A   S   P   V   S   A   A   V   G   G   T   V   T   I AATTGCCAGGCCAGTCAGAGTGTTTATAATGGCAACCGGTTAGGCTGGTATCAGCTGAAA
  N   C   Q   A   S   Q   S   V   Y   N   G   N   R   L   G   W   Y   Q   L   K CCAGGGCAGTCTCCCAAGGAACTGATCCATGATGCATCCACTCTGGCATCTGGGGTCCCA
  P   G   Q   S   P   K   E   L   I   H   D   A   S   T   L   A   S   G   V   P TCGCGGTTTAGAGGCAGTGGATCTGGGACGCAGTTCACTCTCACCATCAACGACGTGCAG
  S   R   F   R   G   S   G   S   G   T   Q   F   T   L   T   I   N   D   V   Q TGTGACGATGCTGCCACCTACTACTGTGTAGGCAGTTATGCCTGTAGTACTGGTGATTGT
  C   D   D   A   A   T   Y   Y   C   V   G   S   Y   A   C   S   T   G   D   C AATGTTTTCGGCGGAGGGACCGAGGTGGTGGTCAAA
  N   V   F   G   G   G   T   E   V   V   V   K Variable Heavy Chain Sequence
(Nucleotide/Peptide, SEQ ID NO: 7/8), 330 nt
CAGTCGGTGGAGGAGTCCGGGGGTCGCCTGGTCACGCCTGGGACACCCCTGACACTCACC
  Q   S   V   E   E   S   G   G   R   L   V   T   P   G   T   P   L   T   L   T TGCAAAGTCTCTGGATTCGACATCAATAGCTATGCAATGGACTGGTTCCGCCAGGCTCCA
  C   K   V   S   G   F   D   I   N   S   Y   A   M   D   W   F   R   Q   A   P GGGAAGGGGCTGGAATGGATCGGAATGATGTCTACTCGTGGTAATACATACTACACGAGC
  G   K   G   L   E   W   I   G   M   M   S   T   R   G   N   T   Y   Y   T   S TGGGCGAAAGGCCGCTTCACCATCTCCAAAACCTCGTCGACCACGGTGGATCTGAAAATG
  W   A   K   G   R   F   T   I   S   K   T   S   S   T   T   V   D   L   K   M ACCAGTCTGACAACCGAGGACACGGCCACTTATTTCTGTGCCAGAGGGGGCTTGTGGGGC
  T   S   L   T   T   E   D   T   A   T   Y   F   C   A   R   G   G   L   W   G

CCAGGCACCCTGGTCACCGTCTCCTCCGGA
  P   G   T   L   V   T   V   S   S   G
```

The selected rabbit monoclonal anti-human Id1, clone #BCH-2/#5-3, in Example 11 had the following DNA and amino acid sequence:

```
Variable Light Chain Sequence
(Nucleotide/Peptide, SEQ ID NO: 9/10), 333 nt
GTATTCGAATTGACCCAGACTCCAGCCTCCGTGGAGGCAGCTGTGGGAGGCACAGTCACC
  V   F   E   L   T   Q   T   P   A   S   V   E   A   A   V   G   G   T   V   T ATCAAGTGCCAGGCCAGTCAGAGCATTAGTAGCTACTTAGCCTGGTATCAGCAGAAACCA
  I   K   C   Q   A   S   Q   S   I   S   S   Y   L   A   W   Y   Q   Q   K   P GGACAGCCTCCCAAGCTCCTGGTCTACAGCGCATCCACTCTGCAATCTGGGGTCCCATCG
  G   Q   P   P   K   L   L   V   Y   S   A   S   T   L   Q   S   G   V   P   S CGGTTCAAAGGCAGTGGATCTGGGACAGACTTCACTCTCACCATCAGCGGCGTGCAGTGT
  R   F   K   G   S   G   S   G   T   D   F   T   L   T   I   S   G   V   Q   C GACGATGCTGCCACTTACTACTGTCAAAGTTATTATGATGGTAGTAGTACTTCTGGTAAT
  D   D   A   A   T   Y   Y   C   Q   S   Y   Y   D   G   S   S   T   S   G   N

GTTTTCGGCGGAGGGACCGAGGTGGTGGTCAAG
  V   F   G   G   G   T   E   V   V   V   K

Variable Heavy Chain Sequence
(Nucleotide/Peptide, SEQ ID NO: 11/12), 375 nt
CAGTCGTTGGAGGAGTCCGGGGGAGACCTGGTCAAGCCTGGGGCATCCCTGACACTCACC
  Q   S   L   E   E   S   G   G   D   L   V   K   P   G   A   S   L   T   L   T TGCACAGCCTCTGGATTCTCCTTCAGTATCAGCTACTATATGTGCTGGGTCCGCCAGGCT
  C   T   A   S   G   F   S   F   S   I   S   Y   Y   M   C   W   V   R   Q   A CCAGGGAAGGGGCCGGAGTGGATCGGATGTATTATTACTGGTAATATTGTCGGCACTTAC
  P   G   K   G   P   E   W   I   G   C   I   I   T   G   N   I   V   G   T   Y

TACGAAAACTGGGCGAAAGGCCGATTCACCATCTCCAAAACCTCGAGCACGGTGACTCTG
```

-continued

```
                  Y  E  N  W  A  K  G  R  F  T  I  S  K  T  S  S  T  V  T  L

CAAATGACCAGTCTGACAGCCGCGGACACGGCCACCTATTTTTGTGCGAGAGGATCTGGT
 Q  M  T  S  L  T  A  A  D  T  A  T  Y  F  C  A  R  G  S  G

AGTGCTAGTGCTGATTATATTGGGATTTACTTTAAGTTGTGGGGCCCAGGCACCCTGGTC
 S  A  S  A  D  Y  I  G  I  Y  F  K  L  W  G  P  G  T  L  V

ACCGTCTCCTCAGGG
 T  V  S  S  G
```

The selected rabbit monoclonal anti-human/mouse Id1, clone #BCH-1/#195-14, had the following DNA and amino acid sequence:

```
Variable Light Chain Sequence
(Nucleotide/Peptide, SEQ ID NO: 13/14), 330 nt
gctgacattgtgatgacccagactccagcctccgtggaggcagctgtggaggcacagtc
 A  D  I  V  M  T  Q  T  P  A  S  V  E  A  A  V  G  G  T  V accatcaagtgccaggccagtgagagcattattaatagattagcctggtatcagcagaaa
 T  I  K  C  Q  A  S  E  S  I  I  N  R  L  A  W  Y  Q  Q  K ccagggcagcctcccaagctcctgatctacagggcatccactctggaatctggggtccca
 P  G  Q  P  P  K  L  L  I  Y  R  A  S  T  L  E  S  G  V  P tcgcggttcaaaggcagtggatctgggacagagttcactctcaccatcagcgacctggag
 S  R  F  K  G  S  G  S  G  T  E  F  T  L  T  I  S  D  L  E tgtgacgatggtgccacttactattgtcaagctactgactatggtgatagttattttact
 C  D  D  G  A  T  Y  Y  C  Q  A  T  D  Y  G  D  S  Y  F  T ttcggcggagggaccgaggtggtggtcaaa
 F  G  G  G  T  E  V  V  V  K Variable Heavy Chain Sequence
(Nucleotide/Peptide, SEQ ID NO: 15/16), 351 nt
cagtcggtggaggagtccgggggtcgcctggtctcgcctggacaccccctgacactcacc
 Q  S  V  E  E  S  G  G  R  L  V  S  P  G  T  P  L  T  L  T tgcacagtctctggattctccctcagttcttttccaatgggctgggtccgccaggctcca
 C  T  V  S  G  F  S  L  S  S  F  P  M  G  W  V  R  Q  A  P gggaaggggctggaatacatcggaatcatgagtactagtggtagcacatactacgcggac
 G  K  G  L  E  Y  I  G  I  M  S  T  S  G  S  T  Y  Y  A  D tgggcgaaaggccgattcaccatctccaaaacctcgtcgaccacgatggatctgaaaatg
 W  A  K  G  R  F  T  I  S  K  T  S  S  T  T  M  D  L  K  M accagtctgacaaccgaggacacggccacctatttctgtgccagaggggctgctagtagg
 T  S  L  T  T  E  D  T  A  T  Y  F  C  A  R  A  A  S  R ttttatgcctttaccttgtggggcccaggcaccctggtcaccgtctcctca
 F  Y  A  F  T  L  W  G  P  G  T  L  V  T  V  S  S
```

Example 13

Cross-reactivity of Rabbit Monoclonal Anti-Mouse Id1, Rabbit Monoclonal Anti-Human Id1, and Rabbit Monoclonal Anti-Mouse/Human Id1 Determined by Western Blot The selected rabbit monoclonal anti-mouse Id1, rabbit monoclonal anti-human Id1, and rabbit monoclonal anti-mouse/human Id1 produced in Examples 10 and 11 were compared with a commercially available rabbit polyclonal anti-mouse/human Id1 from Santa Cruz Biotechnology Inc. (Santa Cruz, Calif.) by Western blot analysis.

The antibodies were tested by western blotting on HeLa (H lane) and 10T1/2 fibroblast whole cell extracts (M lane) at 40 µg per lane. The experiments were performed according to the following procedures:

a. Boil ~40 µg of whole cell extract for ~3 minutes in SDS loading dye. Chill on ice 2 min.
b. Load onto a 15% SDS-polyacrylamid gel and run at 100 V till blue dye is about a cm off the bottom of the gel.
c. Transfer overnight to PVDF membrane at 30 V at 4 C (use COLD transfer buffer).
d. The next day, block 1 hour with 5% milk in PBS at room temp (all subsequent steps at RT).
e. Incubate 1 hour with primary antibody diluted in 1% milk+ PBS+0.05% TWEEN.
f. Wash 3×5 minutes with PBS+0.05% TWEEN.
g. Incubate 30 minutes with secondary antibody (1:5000 dilution of Amersham's anti-rabbit IgG HRP in 1% milk+ PBS+0.05% TWEEN).
h. Wash 3×5 minutes in PBS+0.05% TWEEN.
i. Drain membrane and treat with ECL Plus for 5 minutes j. Expose to film (initial 5-10 second quick exposures). Depending on intensity, expose for 30 seconds/1 minute/5 minutes/10 minutes/1 hour.

In FIG. 1, the rabbit monoclonal anti-mouse Id1, clone #BCH-1/#37-2, of this invention was used to develop blot A. Santa Cruz Biotechnology's rabbit polyclonal anti-mouse/human Id1 was used to develop blot B. The results demonstrate that:

(A) The rabbit monoclonal anti-mouse Id1, clone #BCH-1/#37-2, of this invention detects only mouse Id1 from the transfected cells but not human Id1 from the untransfected cells.

(B) Santa Cruz Biotechnology's rabbit polyclonal anti-mouse/human Id1 detects human Id1 and mouse Id1 as well as endogenous non-Id1 related materials at other molecular weights.

Figures 1, 2:
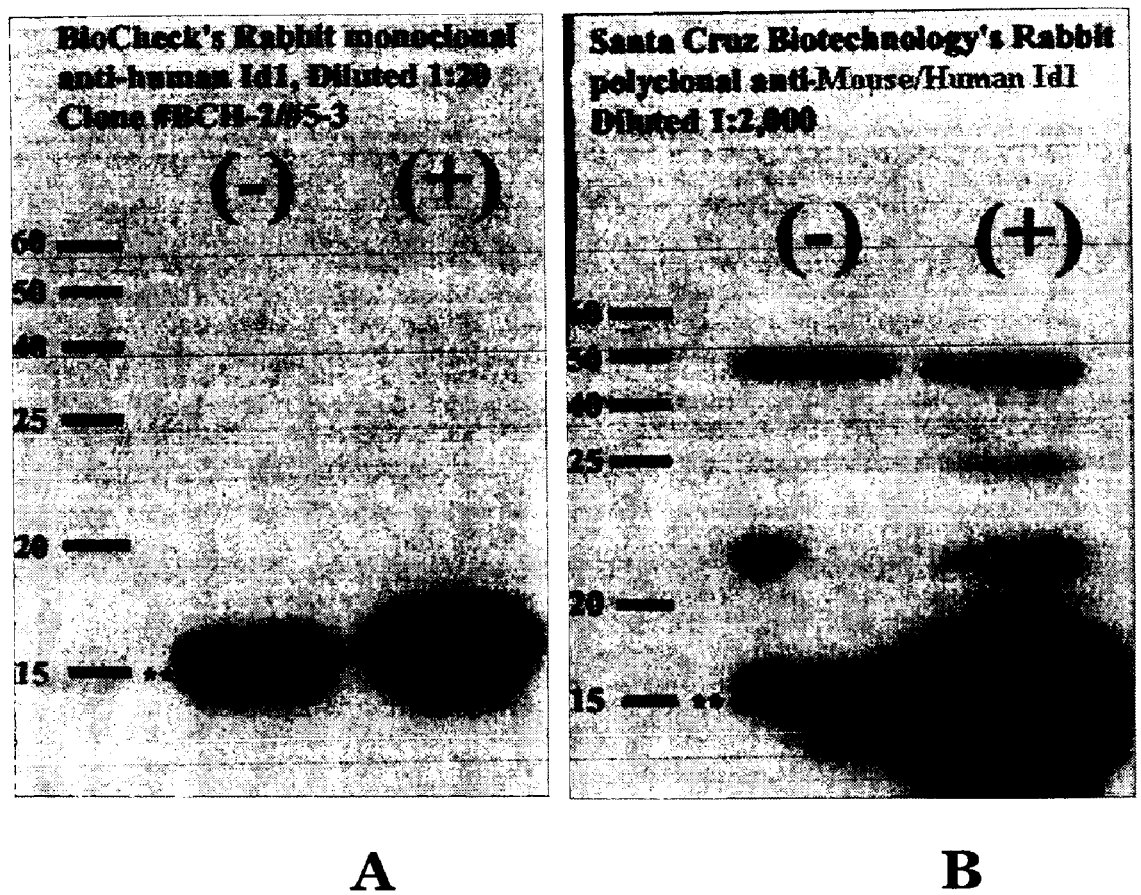
Figure 2:
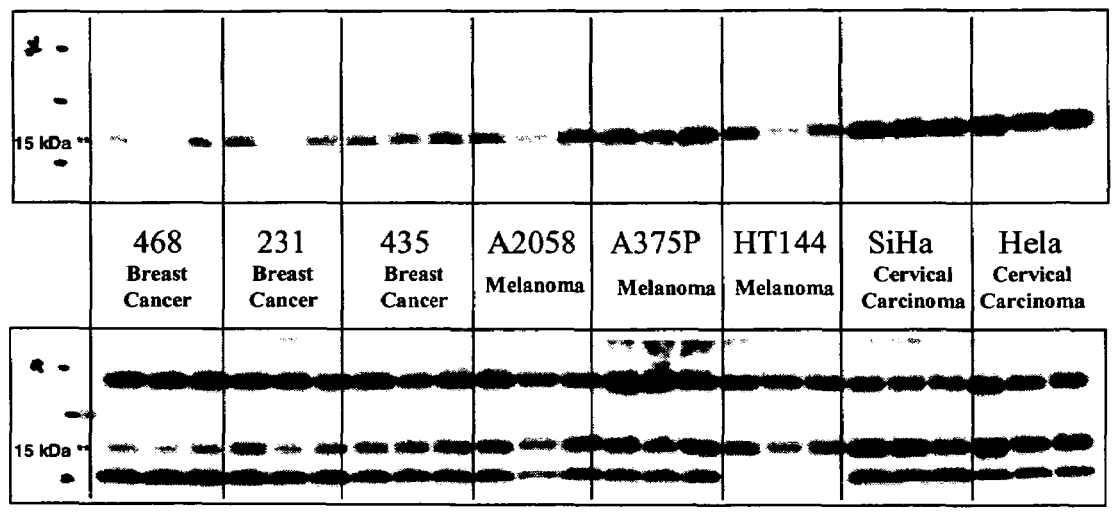

In FIGS. 2-1 and 2-2, the rabbit monoclonal anti-human Id1, clone #BCH-1/#5-3, of this invention was used to develop blot A. Santa Cruz Biotechnology's rabbit polyclonal anti-mouse/human Id1 was used to develop blot B.

The results of FIG. 2-1 demonstrate that:

(A) The rabbit monoclonal anti-human Id1, clone #BCH-1/#5-3, detects human Id from both the untransfected cells and transfected cells.

(B) The Santa Cruz Biotechnology's rabbit polyclonal anti-mouse/human Id1 detects human Id1 in both untransfected cells and human/mouse Id1 in transfected cells as well as endogenous non-Id1 related materials at other molecular weights.

The results of FIG. 2-2 demonstrate that:

(A) The rabbit monoclonal anti-human Id1, clone #BCH-1/#5-3, detects human Id1 specifically in all the tested human cancer cell extracts.

(B) The Santa Cruz Biotechnology's rabbit polyclonal anti-mouse/human Id1 detects human Id1 and non-Id1 proteins of different molecular weight in all the tested human cancer cell extracts.

Figure 3:
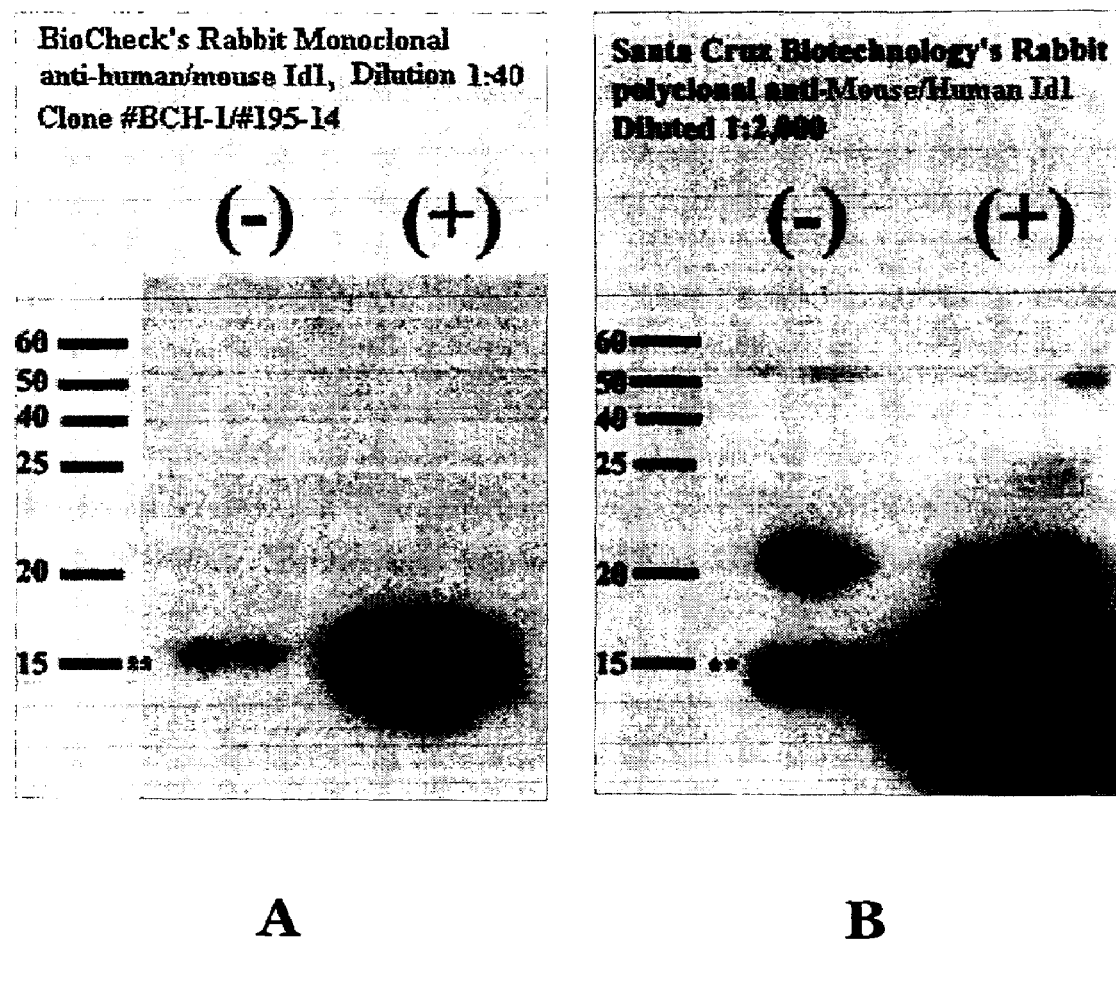
FIG. 3A and 3B are a Western blot analyses of extracts from HeLa cells. Extracts in the (−) lanes are from untransfected cells that express human Id1. Extracts in the (+) lane are cells transfected to express both mouse Id1 and human Id1. The rabbit monoclonal anti-mouse/human Id1, clone #BCH-1/#195-14, of this invention was used to develop blot A. Santa Cruz Biotechnology's rabbit polyclonal anti-mouse/human Id1 was used to develop blot B. In these blots the molecular weight markers are kDa and the MW of Id1, ~15 kDa, is designated with **.

In FIG. 3, the rabbit monoclonal anti-mouse/human Id1, clone #BCH-1/#195-14, of this invention was used to develop blot A. Santa Cruz Biotechnology's rabbit polyclonal anti-mouse/human Id1 was used to develop blot B. The results demonstrate that:

(A) The rabbit monoclonal anti-mouse/human Id1, clone #BCH-1/#195-14, of this invention detects mouse Id1 and human Id from both the untransfected cells and transfected cells.

(B) The Santa Cruz Biotechnology's rabbit polyclonal anti-mouse/human Id1 detects human Id1 in untransfected and human/mouse Id1 in transfected cells as well as endogenous non-Id1 related materials at other molecular weights.

The above results demonstrate that the rabbit monoclonal anti-mouse Id1, clone #BCH-1/#37-2, anti-human Id1, clone #BCH-2/#5-3, and anti-mouse/human Id1, clone #BCH-1/#195-14 of this invention are selective for the particular Id1 protein that is specific to the target species (mouse alone, human alone, and mouse/human respectively) and show no substantial reactivity towards endogenous proteins. Conversely, the rabbit polyclonal anti-mouse/human Id1 from Santa Cruz Biotechnology is not specific to human Id1 or mouse Id1, and reacts with other endogenous proteins.

Example 14

Selectivity of Rabbit Monoclonal Anti-Mouse Id1, Rabbit Monoclonal Anti-Human Id1, and Rabbit Monoclonal Anti-Mouse/Human Id1 Determined by ELISA The rabbit monoclonal anti-mouse Id1 (clone #BCH-1/#37-2), the rabbit monoclonal anti-human Id1 (clone #BCH-2/#5-3), and the rabbit monoclonal anti-mouse/human Id1 (clone #BCH-1/#195-14) produced in Examples 10 and 11 were screened for reactivity against the following antigens: mouse Id1:His, human Id1:His, mouse Id2:His, human Id2:His, mouse Id3:His, human Id3:His, mouse Id4:His, and human Id4:His.

Materials:

1. Microtiter wells were coated (0.1 μg/well) with mouse Id1:His, human Id1:His, mouse Id2:His, human Id2:His, mouse Id3:His, human Id3:His, and mouse Id4:His, human Id4:His.

2. Antibody Diluent: 0.25% (w/v) BSA in 0.015M KPO4 Buffer, 0.85% (w/v) NaCl, 0.1% (w/v) NaN$_3$, pH=7.40.

3. Rabbit monoclonal anti-mouse Id1 (clone #37-2; Protein G purified), was diluted to 0.005, 0.010, 0.025, 0.05, 0.10, 0.25, and 0.50 μg/ml with the antibody diluent.

4. Rabbit monoclonal anti-human Id1 (clones #5-3; Protein G purified), was diluted to 0.005, 0.010, 0.025, 0.05, 0.10, 0.25, and 0.50 μg/ml with the antibody diluent.

5. Rabbit monoclonal anti-mouse/human Id1 (clone #195-14; Protein G purified), was diluted to 0.005, 0.010, 0.025, 0.05, 0.10, 0.25, and 0.50 μg/ml with the antibody diluent.

6. Conjugate Diluent: 50% (v/v) Fetal Bovine Serum in 0.05 M Tris, 1% (v/v) Proclin-300, pH 7.6.

7. Conjugate: Goat anti-rabbit IgG (H+L)–HRP conjugate.

8. TMB reagent.

9. Stop solution (1 N HCl).

Assay Protocols:

1. Secure the desired number of coated wells in the holder.

2. Dispense 100 μL of antibody diluent (as blank) and diluted antibody.

3. Incubate at room temperature with mechanical shaking for 90 minutes; speed=750 rpm.

4. Remove the incubation mixture by flicking plate content into an appropriate waste container, followed by rinsing the wells 5 times with distilled water.

5. Strike the wells sharply onto absorbent paper or paper towels to remove all residual water droplets.

6. Dispense 100 μL of 1:50,000 Enzyme Conjugate Reagent into each well. Gently mix for 5 seconds.

7. Incubate at room temperature with mechanical shaking for 90 minutes; speed=750 rpm.

8. Repeat procedures 4 and 5.

9. Dispense 100 μL of TMB Reagent into each well. Gently mix for 5 seconds.

10. Incubate at room temperature with mechanical shaking for 20 minutes; speed=750 rpm.

11. Add 100 μL of Stop Solution (1N HCl) into each well.

12. Gently mix for 10 seconds to ensure a complete mixing.

13. Read OD at A450.

Tables 5-1 to 5-8 show the results of rabbit monoclonal antibodies, anti-mouse Id1 (#37-2), anti-human Id1 (#5-13), and anti-mouse/anti-human Id1 (#195-14) on binding to (1) Mouse Id1:His Antigen-coated wells, (2) Human Id1:His Antigen-coated wells, (3) Mouse Id2: His Anitgen-coated wells, (4) Human Id2: His Antigen-coated wells, (5) Mouse Id3: His Antigen-coated wells, (6) Human Id3: His Antigen-coated wells, (7) Mouse Id4: His Antigen-coated wells, (8) Human Id4: His Antigen-coated wells.

TABLE 5-1

Mouse Id1:His-coated wells

Id1 MoAbs

| Ab Conc. (μg/ml) | m Id1 MoAb 37-2 $A_{450}$ | h Id1 MoAb 5-3 $A_{450}$ | m/h Id1 MoAb 195-14 $A_{450}$ |
|---|---|---|---|
| 0.000 | 0.048 | 0.046 | 0.045 |
| 0.005 | 0.310 | 0.063 | 0.249 |
| 0.010 | 0.571 | 0.068 | 0.424 |
| 0.025 | 1.127 | 0.053 | 0.876 |
| 0.050 | 1.841 | 0.057 | 1.393 |
| 0.100 | 2.536 | 0.068 | 2.035 |
| 0.250 | 3.404 | 0.092 | 2.571 |
| 0.500 | 3.814 | 0.151 | 2.785 |

TABLE 5-2

Human Id1:His-coated wells

Id1 MoAbs

| Ab Conc. (μg/ml) | m Id1 MoAb 37-2 $A_{450}$ | h Id1 MoAb 5-3 $A_{450}$ | m/h Id1 MoAb 195-14 $A_{450}$ |
|---|---|---|---|
| 0.000 | 0.051 | 0.052 | 0.050 |
| 0.005 | 0.057 | 0.209 | 0.310 |
| 0.010 | 0.056 | 0.362 | 0.569 |
| 0.025 | 0.073 | 0.728 | 1.117 |
| 0.050 | 0.092 | 1.223 | 1.697 |
| 0.100 | 0.117 | 1.857 | 2.165 |
| 0.250 | 0.187 | 2.761 | 2.883 |
| 0.500 | 0.270 | 3.154 | 3.025 |

TABLE 5-3

Mouse Id2:His-coated wells

Id1 MoAbs

| Ab Conc. (μg/ml) | m Id1 MoAb 37-2 $A_{450}$ | h Id1 MoAb 5-3 $A_{450}$ | m/h Id1 MoAb 195-14 $A_{450}$ |
|---|---|---|---|
| 0.000 | 0.057 | 0.051 | 0.051 |
| 0.005 | 0.050 | 0.048 | 0.052 |
| 0.010 | 0.055 | 0.049 | 0.048 |
| 0.025 | 0.055 | 0.048 | 0.049 |
| 0.050 | 0.082 | 0.050 | 0.054 |
| 0.100 | 0.074 | 0.049 | 0.054 |
| 0.250 | 0.097 | 0.052 | 0.053 |
| 0.500 | 0.134 | 0.049 | 0.057 |

TABLE 5-4

Human Id2:His-coated wells

Id1 MoAbs

| Ab Conc. (μg/ml) | m Id1 MoAb 37-2 $A_{450}$ | h Id1 MoAb 5-3 $A_{450}$ | m/h Id1 MoAb 195-14 $A_{450}$ |
|---|---|---|---|
| 0.000 | 0.058 | 0.049 | 0.058 |
| 0.005 | 0.054 | 0.049 | 0.048 |
| 0.010 | 0.056 | 0.046 | 0.054 |
| 0.025 | 0.060 | 0.049 | 0.050 |
| 0.050 | 0.064 | 0.048 | 0.048 |
| 0.100 | 0.080 | 0.054 | 0.053 |
| 0.250 | 0.109 | 0.056 | 0.057 |
| 0.500 | 0.160 | 0.062 | 0.072 |

TABLE 5-5

Mouse Id3:His-coated wells

Id1 MoAbs

| Ab Conc. (μg/ml) | m Id1 MoAb 37-2 $A_{450}$ | h Id1 MoAb 5-3 $A_{450}$ | m/h Id1 MoAb 195-14 $A_{450}$ |
|---|---|---|---|
| 0.000 | 0.062 | 0.058 | 0.050 |
| 0.005 | 0.048 | 0.047 | 0.048 |
| 0.010 | 0.051 | 0.048 | 0.047 |
| 0.025 | 0.047 | 0.046 | 0.047 |
| 0.050 | 0.057 | 0.052 | 0.050 |
| 0.100 | 0.052 | 0.050 | 0.050 |
| 0.250 | 0.054 | 0.050 | 0.049 |
| 0.500 | 0.062 | 0.050 | 0.051 |

TABLE 5-6

Human Id3:His-coated wells

Id1 MoAbs

| Ab Conc. (μg/ml) | m Id1 MoAb 37-2 $A_{450}$ | h Id1 MoAb 5-3 $A_{450}$ | m/h Id1 MoAb 195-14 $A_{450}$ |
|---|---|---|---|
| 0.000 | 0.063 | 0.052 | 0.049 |
| 0.005 | 0.047 | 0.048 | 0.047 |
| 0.010 | 0.048 | 0.044 | 0.048 |
| 0.025 | 0.053 | 0.046 | 0.047 |
| 0.050 | 0.059 | 0.046 | 0.047 |
| 0.100 | 0.064 | 0.046 | 0.047 |
| 0.250 | 0.071 | 0.048 | 0.052 |
| 0.500 | 0.081 | 0.052 | 0.053 |

TABLE 5-7

Mouse Id4: His-coated wells

Id1 MoAbs

| Ab Conc. (μg/ml) | m Id1 MoAb 37-2 $A_{450}$ | h Id1 MoAb 5-3 $A_{450}$ | m/h Id1 MoAb 195-14 $A_{450}$ |
|---|---|---|---|
| 0.000 | 0.047 | 0.045 | 0.047 |
| 0.005 | 0.048 | 0.045 | 0.047 |
| 0.010 | 0.052 | 0.043 | 0.045 |

TABLE 5-7-continued

Mouse Id4: His-coated wells

Id1 MoAbs

| Ab Conc. (μg/ml) | m Id1 MoAb 37-2 $A_{450}$ | h Id1 MoAb 5-3 $A_{450}$ | m/h Id1 MoAb 195-14 $A_{450}$ |
|---|---|---|---|
| 0.025 | 0.047 | 0.047 | 0.046 |
| 0.050 | 0.048 | 0.048 | 0.049 |
| 0.100 | 0.049 | 0.049 | 0.049 |
| 0.250 | 0.053 | 0.053 | 0.048 |
| 0.500 | 0.052 | 0.050 | 0.049 |

TABLE 5-8

Human Id4: His-coated wells

Id1 MoAbs

| Ab Conc. (μg/ml) | m Id1 MoAb 37-2 $A_{450}$ | h Id1 MoAb 5-3 $A_{450}$ | m/h Id1 MoAb 195-14 $A_{450}$ |
|---|---|---|---|
| 0.000 | 0.047 | 0.046 | 0.046 |
| 0.005 | 0.048 | 0.049 | 0.044 |
| 0.010 | 0.046 | 0.045 | 0.046 |
| 0.025 | 0.045 | 0.049 | 0.045 |
| 0.050 | 0.050 | 0.052 | 0.049 |
| 0.100 | 0.061 | 0.047 | 0.049 |
| 0.250 | 0.050 | 0.047 | 0.048 |
| 0.500 | 0.052 | 0.056 | 0.048 |

Tables 6-1 to 6-3 summarize the cross-reactivity of (1) rabbit monoclonal anti-mouse Id1 (#37-2), (2) rabbit monoclonal anti-human Id1 (#5-3), and (3) rabbit monoclonal anti-mouse Id1 /anti-human Id1 (#195-14) toward Id proteins.

TABLE 6-1

Cross-reactivity of rabbit monoclonal anti-mouse Id1 (#37-2) toward Id proteins

| Protein | Cross-reactivity (%) |
|---|---|
| Mouse Id1 | 100 |
| Human Id1 | <1.0 |
| Mouse Id2, Human Id2 | <1.0 |
| Mouse Id3, Human Id3 | <1.0 |
| Mouse Id4, Human Id4 | <1.0 |

TABLE 6-2

Cross-reactivity of rabbit monoclonal anti-human Id1 (#5-3) toward Id proteins

| Protein | Cross-reactivity (%) |
|---|---|
| Mouse Id1 | <1.0 |
| Human Id1 | 100 |
| Mouse Id2, Human Id2 | <1.0 |
| Mouse Id3, Human Id3 | <1.0 |
| Mouse Id4, Human Id4 | <1.0 |

TABLE 6-3

Cross-reactivity of rabbit monoclonal anti-mouse Id1/anti-human Id1 (#195-14) toward Id proteins

| Protein | Cross-reactivity (%) |
|---|---|
| Mouse Id1 | 100 |
| Human Id1 | 100-150 |
| Mouse Id2, Human Id2 | <1.0 |
| Mouse Id3, Human Id3 | <1.0 |
| Mouse Id4, Human Id4 | <1.0 |

Conclusions:

1. Rabbit monoclonal anti-mouse Id1 (#37-2) had very high ELISA bindings against mouse Id1 but no cross reactivity (<1%) with human Id1, mouse/human Id2, mouse/human Id3 or mouse/human Id4.
2. Rabbit monoclonal anti-human Id1 (#5-3) had very high ELISA bindings against human Id1 but no cross reactivity (<1%) with mouse Id1, mouse/human Id2, mouse/human Id3 or mouse/human Id4.
3. Rabbit monoclonal anti-mouse/human Id1 (#195-14) had very high ELISA bindings against mouse Id1 and human Id1 but no cross reactivity (<1%) with mouse/human Id2, mouse/human Id3 or mouse/human Id4.

Example 15

Comparison Analysis by Immunohistochemistry (IHC) of the Same Mouse Mammary Tumor Tissue by Either the Rabbit Monoclonal Anti-Mouse Id1 or a Commercially Available Mouse Monoclonal Anti-Mouse Id1

Comparison of the rabbit monoclonal anti-mouse Id1, clone# BCH-1/#37-2, of this invention of Example 10 was made with mouse monoclonal anti-mouse Id1 from BD Pharmingen, San Diego, Calif.

Figure 4:
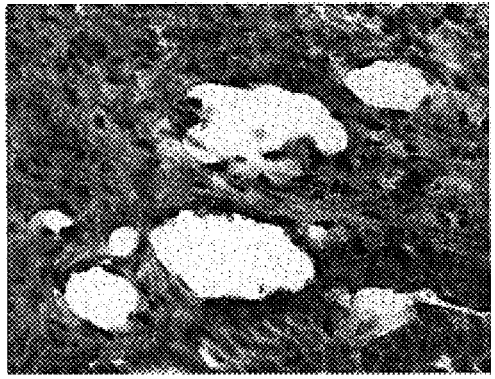
FIG. 4A-4D are an IHC comparison using rabbit monoclonal anti-mouse Id1 and BD Pharmingen's mouse monoclonal anti-mouse Id1. The tissues used were mammary tumor tissue from either a wild-type (Id1$^{+/+}$) mouse or an Id1 knockout (Id1$^{-/-}$) mouse. One set of tissue was treated with the rabbit monoclonal anti-mouse Id1, clone #BCH-1/#37-2 of this invention (A and B) and then developed with goat polyclonal anti-rabbit IgG-HRP conjugate. The other set (C and D) was treated with Pharmingen's mouse monoclonal anti-mouse Id1 and then developed with goat polyclonal anti-mouse IgG-HRP conjugate.
Figure 4:
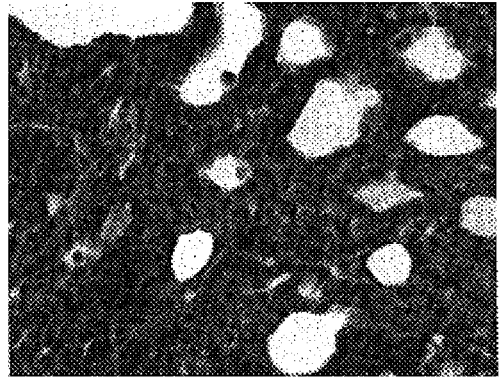
Figure 4:
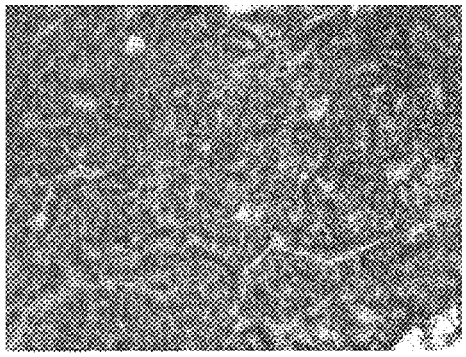
Figure 4:
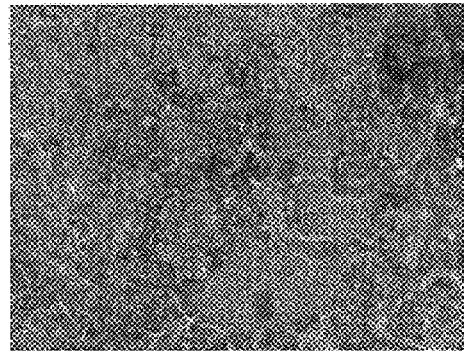

Tissue from mouse mammary tumors from either wild-type ($Id1^{+/+}$) and Id1 knockout mice ($Id1^{-/-}$) were obtained as described in de Candia et al., *Proc Natl Acad Sci USA;* 100: 12337-12342 (2003). In FIG. 4, IHC measurements of the tissue were separately accomplished by rabbit monoclonal anti-mouse Id1, clone# BCH-1/#37-2, of this invention (A and B) followed by goat polyclonal anti-rabbit IgG-HRP conjugate to detect the antibody; or by Pharmingen's mouse monoclonal anti-mouse Id1 (C and D) followed by goat anti-mouse IgG-HRP conjugate to detect the antibody. The results in FIG. 4 demonstrate:

1. Specific Id1 staining was observed with the rabbit monoclonal anti-mouse Id1, clone# BCH-1/#37-2, in cell nucleus of the wild-type mouse ($Id1^{+/+}$) expected to express Id1 (A), and no Id1 staining was observed in the knockout mouse ($Id1^{+/+}$) (B).
2. No staining was observed with the Pharmingen's mouse monoclonal anti-mouse Id1 (C and D).

These results indicated that the rabbit monoclonal anti-mouse Id1 was suitable for IHC use, whereas Pharmingen's mouse monoclonal anti-mouse Id1 was not suitable for IHC use.

Example 16

Analysis by Immunohistochemistry (IHC) of Mouse Mammary Tumor Tissue and Human Mammary Tumor Tissue by Rabbit Monoclonal Anti-Mouse/Human Id1

Figure 5:
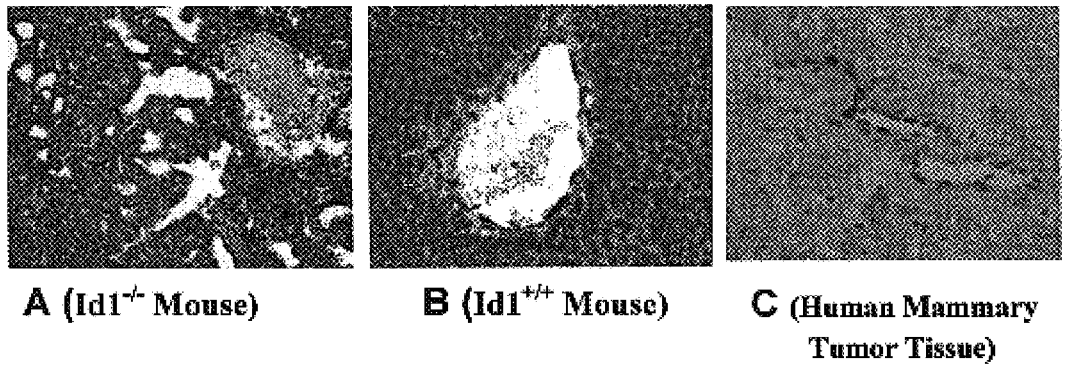
FIG. 5A-5F are an IHC comparison using rabbit monoclonal anti-mouse/human Id1 and Santa Cruz's rabbit polyclonal anti-mouse/human Id1. Both antibodies were used to detect mouse Id1 and human Id1 in IHC. Mammary tumor tissues from an Id1 knockout (Id1$^{-/-}$) mouse (A and D), a wild-type (Id1$^{+/+}$) mouse (B and E), or a human mammary tumor tissue (C and F) were treated with either BioCheck's rabbit monoclonal anti-mouse/human Id1, clone #BCH-I/#195-14 of this invention (A, B and C) or Santa Cruz's rabbit polyclonal anti-mouse/human Id1 (D, E, and F). The tissue sections were then developed with goat polyclonal anti-rabbit IgG-HRP conjugate.
Figure 5:
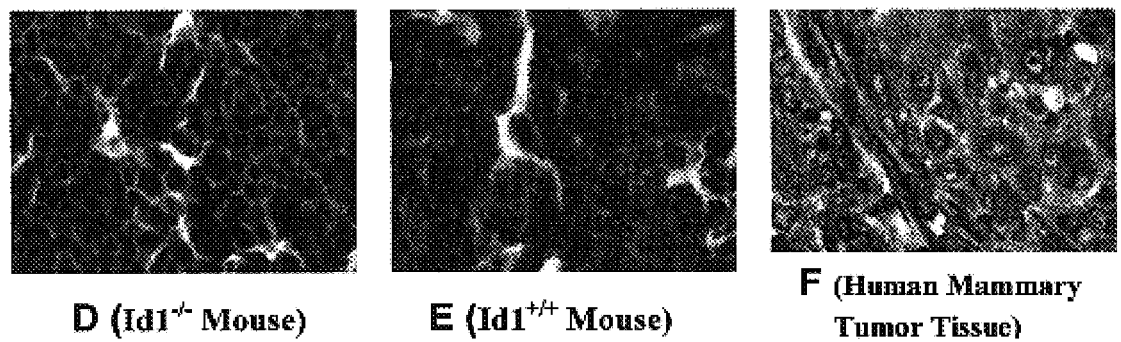
Figure 6:
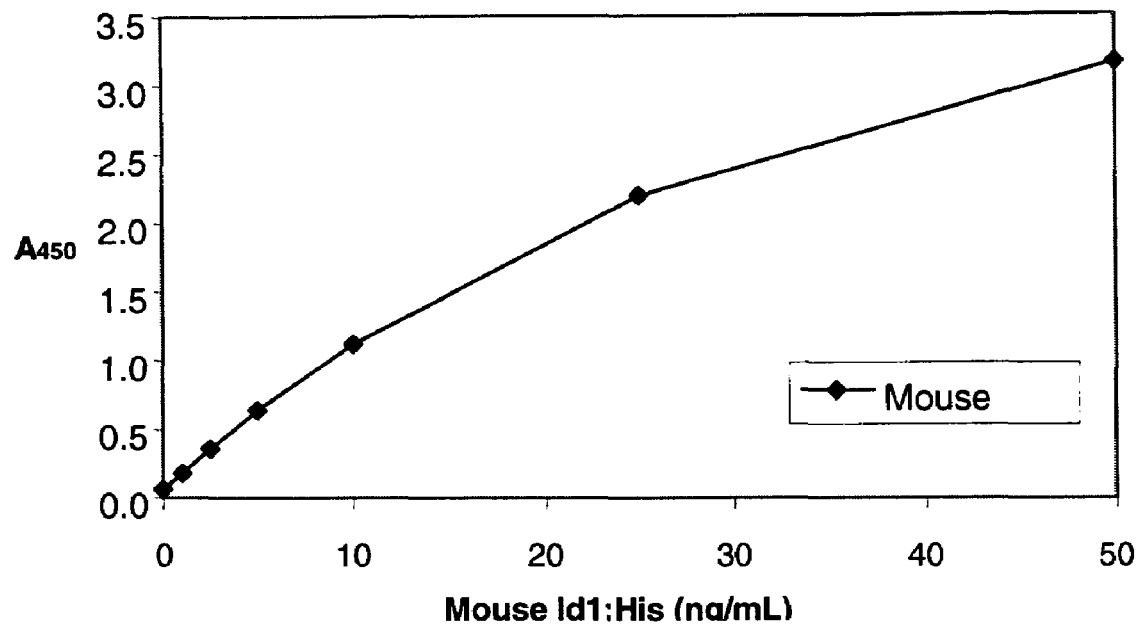
FIG. 6A and 6B are calibration curves obtained following addition of known amounts of mouse Id1: His (A) or human Id1: His (B) to buffered bovine serum albumin and analyzing the resulting solutions using either rabbit anti-mouse Id1(A) of this invention or rabbit anti-human Id1 (B) of this invention in a standard ELISA format. The amount of Id1 antigen bound to the Id1 antibody-coated microtiter wells was detected with rabbit anti-mouse Id1-HRP conjugate or rabbit anti-human Id1-HRP conjugate followed by treatment with TMB and 1N HCl and measurement of optical density at 450 nm.
Figure 6:
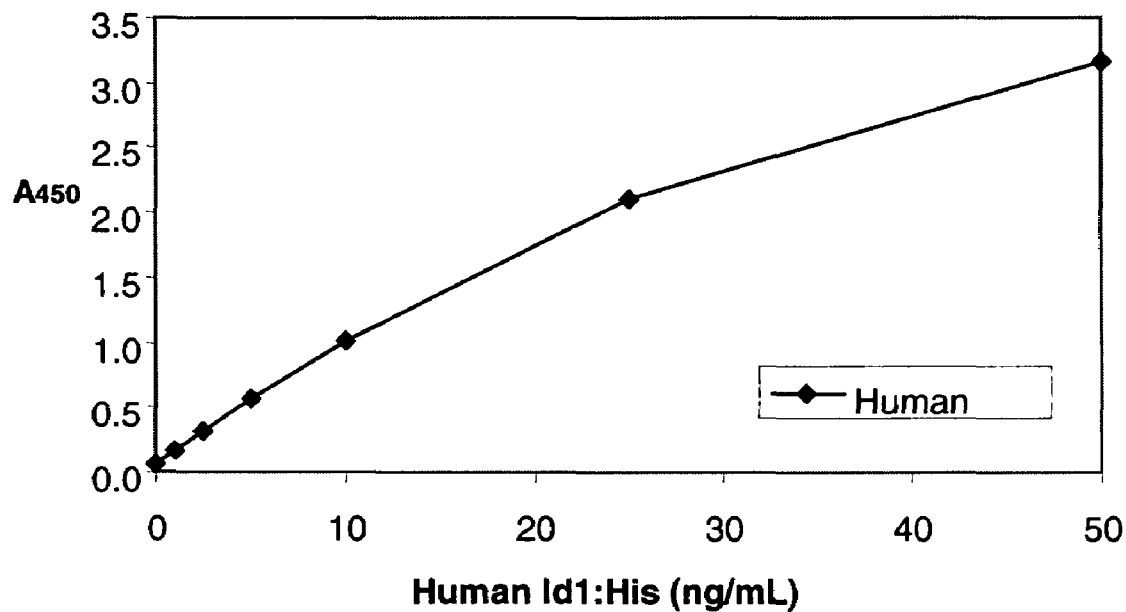

FIG. 5 is an IHC comparison using rabbit monoclonal anti-mouse/human Id1 of this invention and Santa Cruz's rabbit polyclonal anti-mouse/human Id1. Both antibodies were used to detect mouse Id1 and human Id1 in IHC. Mammary tumor tissues from an Id1 knockout (Id1$^{-/-}$) mouse (A and D), a wild-type (Id1$^{+/+}$) mouse (B and E), and a human mammary tumor tissue (C and F), were treated with either BioCheck's rabbit monoclonal anti-mouse/human Id1, clone #BCH-1/#195-14 of this invention (A, B and C) or Santa Cruz's rabbit polyclonal anti-mouse/human Id1 (D, E, and F). The tissue sections were then developed with goat polyclonal anti-rabbit IgG-HRP conjugate. The results in FIG. 5 are summarized as follows.

Rabbit monoclonal anti-mouse/human Id1:
A. No mouse Id1 staining in the Id1 knockout (Id1$^{-/-}$) mouse mammary tumor tissue section.
B. Specific mouse Id1 staining observed in cell nucleus of wild-type (Id1$^{+/+}$) mouse mammary tumor tissue section expected to express mouse Id1.
C. Specific human Id1 staining observed in nucleus of endothelial cells of human mammary tumor tissue section.

Commercial rabbit polyclonal anti-mouse/human Id1:
D. Non-specific staining observed in the Id1 knockout (Id1$^{-/-}$) mouse mammary tumor tissue section.
E. Non-specific/Non-nuclear staining observed in the Id1 wild-type (Id1$^{+/+}$) mouse mammary tumor tissue section.
F. Non-specific/Non-nuclear staining observed in the human mammary tumor tissue section.

Example 17

Comparison by ELISA of Rabbit Monoclonal Anti-Mouse Id1 to a Commercially Available Mouse Monoclonal Anti-Mouse Id1

A comparison was carried out between the reactivity of the rabbit monoclonal anti-mouse Id1, clone #BCH-1/#37-2, of this invention and the mouse monoclonal anti-mouse/human Id1 from BD Pharmingen with the following antigens prepared in Example 5: mouse Id1:His, human Id1:His, human Id2:His, human Id3:His, and GST. These antigens and protein were used to coat the wells.

Materials and methods were those described in Example 9 except (a) Pharmingen's mouse monoclonal anti-mouse Id1 was used in addition to the rabbit monoclonal anti-mouse Id1 (Example 10), and (b) goat anti-mouse IgG-HRP conjugate was used to process the wells treated with the Pharmingen monoclonal antibody and polyclonal goat anti-rabbit IgG-HRP conjugate was used to process wells treated with rabbit monoclonal anti-mouse Id1.

Data from this study are given in Tables 7 and 8 below.

TABLE 7

| | Rabbit Monoclonal Anti-Mouse Id1 (#37-2) | | | | |
|---|---|---|---|---|---|
| Antibody Conc. (µg/ml) | Mouse Id1:His Plate $A_{450}$ | Human Id1:His Plate $A_{450}$ | Human Id2:His Plate $A_{450}$ | Human Id3:His Plate $A_{450}$ | GST Plate $A_{450}$ |
| 0 | 0.047 | 0.047 | 0.045 | 0.046 | 0.047 |
| 0.10 | 1.291 | 0.061 | 0.049 | 0.048 | 0.047 |
| 0.25 | 1.996 | 0.070 | 0.049 | 0.047 | 0.051 |
| 0.50 | 2.463 | 0.091 | 0.052 | 0.052 | 0.053 |
| 1.00 | 2.878 | 0.113 | 0.053 | 0.063 | 0.062 |
| 2.50 | 3.163 | 0.132 | 0.070 | 0.069 | 0.068 |
| 5.00 | 3.258 | 0.153 | 0.083 | 0.091 | 0.086 |
| 10.0 | 3.275 | 0.194 | 0.115 | 0.113 | 0.108 |

TABLE 8

| | BD Pharmingen Mouse Monoclonal Anti-Mouse Id1 | | | | |
|---|---|---|---|---|---|
| Antibody Conc. (µg/ml) | Mouse Id1:His Plate $A_{450}$ | Human Id1:His Plate $A_{450}$ | Human Id2:His Plate $A_{450}$ | Human Id3:His Plate $A_{450}$ | GST Plate $A_{450}$ |
| 0 | 0.050 | 0.054 | 0.050 | 0.051 | 0.050 |
| 0.10 | 0.239 | 0.316 | 0.052 | 0.053 | 0.060 |
| 0.25 | 0.496 | 0.771 | 0.057 | 0.060 | 0.065 |
| 0.50 | 0.848 | 1.253 | 0.063 | 0.067 | 0.077 |
| 1.00 | 1.340 | 1.826 | 0.082 | 0.089 | 0.093 |
| 2.50 | 2.054 | 2.284 | 0.105 | 0.114 | 0.092 |
| 5.00 | 2.478 | 2.835 | 0.160 | 0.161 | 0.118 |
| 1.0 | 2.937 | 3.125 | 0.184 | 0.156 | 0.108 |

Both types of antibodies showed strong ELISA binding against mouse Id1. The mouse monoclonal anti-mouse Id1 from BD Pharmingen also bound strongly with human Id1. However, the mouse monoclonal anti-mouse Id1 from BD Pharmingen did not show IHC staining with the wild-type (Id$^{+/+}$) mouse mammary tumor tissue as shown in FIG. 4. The rabbit monoclonal anti-mouse Id1, clone #BCH-1/#37-2, had very specific ELISA binding activity and IHC staining against mouse Id1, but with no substantial cross-reactivity with human Id1. Neither monoclonal antibody had substantial cross reactivity with human Id2, human Id3 or GST.

Example 18

ELISA Sandwich Assay (a) Rabbit monoclonal anti-mouse Id1 (#37-2), and (b) rabbit monoclonal anti-human Id1 (#5-3) were used in ELISA sandwich assays.

Materials
1. Microtiter wells: Coated with (a) rabbit monoclonal anti-mouse Id1 (#37-2), or (b) rabbit monoclonal anti-human Id1 (#5-3).
2. Conjugate: Rabbit polyclonal anti-mouse/human Id1 (B-5133)-HRP. The polyclonal antibody was affinity purified by an Id1 antigen affinity column chromatography.
3. Standards: (a) Mouse Id1:His, or (b) Human Id1:His prepared in fetal bovine serum, lyophilized.

4. Conjugate Diluent: 50% (v/v) fetal bovine serum in 0.05 M Tris buffer containing 1% (v/v) Proclin-300, pH 7.60
5. TMB Reagent
6. 1 N HCl as Stop Solution Procedure A. Preparation of Working Conjugate Rabbit polyclonal anti-mouse/human Id1 (B-5133)-HRP was dilulted 1:20,000 for (a), and 1:12,000 for (b).

B. Reagent Preparation

Lyophilized standards need to be reconstituted with 1.0 mL distilled water and allow the reconstituted material to stand for at least 20 minutes at room temperature with gentle mixing before assay.

C. Assay

1. Secure the desired number of separate (a) rabbit anti-mouse Id1, or (b) rabbit anti-human Id1 (either polyclonal or monoclonal) coated wells in the holder.
2. Separately pipette 100 μL of (a) mouse Id1 or (b) human Id1 protein standards into appropriate wells.
3. Thoroughly mix for 30 seconds.
4. Incubate at room temperature (18~25° C.) for 90 minutes with mechanical shaking at 750 rpm.
5. Remove the incubation mixture by emptying the plate contents into a waste container.
6. Rinse and empty the microtiter plate 5 times with distilled water. Strike the microtiter plate sharply onto absorbent paper or paper towels to remove all residual water droplets.
7. Dispense 100 μL of rabbit polyclonal anti-mouse/human Id1 (B-5133)-HRP into each well.
8. Thoroughly mix for 30 seconds.
9. Incubate at room temperature (18~25° C.) for 90 minutes with mechanical shaking at 750 rpm.
10. Repeat Step 5 and 6.
11. Dispense 100 μL of TMB into each well.
12. Mix gently for 5 seconds.
13. Incubate at room temperature (18~25° C.) for 20 minutes with mechanical shaking at 750 rpm.
14. Dispense 100 μL of 1 N HCl into each well.
15. Mix well for 30 seconds.
16. Read absorbance at 450 nm with a microtiter well reader within 15 minutes The absorbance results are shown in Table 9 below for (a) mouse Id1 and (b) human Id1 assays.

TABLE 9a

Mouse Id1 ELISA (Poly/Mono)

| Mouse Id1: His (ng/ml) | $A_{450}$ |
|---|---|
| 0 | 0.053 |
| 0.5 | 0.090 |
| 1.0 | 0.131 |
| 2.5 | 0.270 |
| 5.0 | 0.486 |
| 10.0 | 0.920 |
| 25.0 | 2.142 |
| 50.0 | 2.859 |

TABLE 9b

Human Id1 ELISA (Poly/Mono)

| Human Id1: His (ng/ml) | $A_{450}$ |
|---|---|
| 0 | 0.046 |
| 0.5 | 0.085 |
| 1.0 | 0.124 |
| 2.5 | 0.244 |
| 5.0 | 0.365 |
| 10.0 | 0.815 |
| 25.0 | 1.941 |
| 50.0 | 3.152 |

This example demonstrates that the calibration curves obtained using the rabbit monoclonal anti-mouse Id1 (#37-2) and rabbit monoclonal anti-human Id1 (#5-3) possess suitable sensitivity and dynamic range for the measurement of Id1 in human samples or samples from test systems such as mouse models of human cancer or systems, which evaluate the ability of chemicals to modulate Id1 gene expression or Id1 protein activity.

Example 19

Preparing HRP Conjugate of Rabbit Anti-Human Id1

HRP-conjugated rabbit polyclonal anti-Id1, rabbit monoclonal anti-human Id1, rabbit monoclonal anti-mouse Id1, and rabbit monoclonal anti-human/mouse Id1, are prepared.

Materials

1. The conjugation is performed with rabbit anti-Id1 (polyclonal or monoclonal).
2. HRP is obtained as a powder from Zymed Laboratories, South San Francisco, Calif.
3. S-300 column is hand-packed using gel obtained from Pharmacia.
4. Remaining chemicals and BSA are standard laboratory reagents.

Procedure

1. Dissolve 6.0 mg horseradish peroxidase (HRP) in 1.50 ml distilled water.
2. Add 0.30 ml freshly made 100 mM $NaIO_4$ and stir for 25 minutes at room temperature in the dark.
3. Dialyze the HRP solution at 4° C., for 16-24 hours, in the dark against 1 mM sodium acetate buffer, pH 4.4.
4. Dialyze 6.0 mg/1.50 ml of rabbit anti- Id1 at 4° C, for 16~24 hours, against 0.01 M sodium bicarbonate buffer, pH 9.6.
5. To the dialyzed HRP solution, add 0.06 ml 200 mM carbonate buffer, pH 9.5, and then add the dialyzed rabbit anti-Id1 (from step #4).
6. Stir for 3 hours at room temperature in the dark.
7. Dialyze the antibody-HRP conjugate, in the dark, against 4,000 ml of 0.05 M potassium phosphate buffer, pH 7.20, containing 0.85% NaCl, at 2-8° C. for 16-24 hours.
8. Purify the antibody-HRP conjugate using an S-300 column (2.5 cm×100 cm).
9. Collect the desired fractions.
10. Add BSA (0.25% w/v), polyvinylpyrolidone (PVP, 0.25% w/v), and 0.001% (v/v) Proclin-300 to stabilize the conjugate.
11. Store the rabbit anti-human Id1-HRP conjugate at 2-8° C.

Example 20

Determining Equilibrium Association Constant

Biacore Protocol & Experimental Conditions

Antibodies were immobilized on CM5 sensor chips. All SPR (surface plasmon resonance) assays were carried out in a BIACORE 2000 instrument. A mouse monoclonal antibody was used as reference labeled at the 2nd channel (Fc2) of the chip. BCH-1#37-2 was immobilized on the 4th (Fc4) channel. Final conjugation of antibodies on chip surface was 1878 RU for BCH-1#37-2. Mouse Id-1 and human Id-1 were applied as mobile analytes. The binding assays were carried out in HBS-P buffer (10 mM HEPES, pH 7.4, containing 150 mM sodium chloride, 0.005% surfactant P-20 detergent and 0.12% glycerol). Kinetics were determined with 8 different analyte concentrations ranging from 3.4 riM to 573 nM. For analyses, 125 µl of analyte were injected (Kinject protocol) at 30 µl/min and the dissociation lasted for 240 seconds at the same flow rate. The surface was regenerated by washing with 50 µl solution of 100 mM glycine and 100 mM of HCl, pH 1.81, at 60 µl/min and the extra cleaning protocol was followed. The kinetic analyses of sensograms were based on the Langmuir (1:1) binding model. Both association rate constant and dissociation rate constants for the interaction of mouse Id-1 and human Id-1 with the immobilized antibodies were determined from the analysis of sensograms using the Biaevaluation software, version 3.0. All binding curves were corrected for background and bulk refractive index contribution by subtraction of the reference flow cells. Models were fitted globally across the data sets. All experiments and analyses were duplicated.

Results

The equilibrium association constant $K_D$ (binding constant) of antibody BCH-1#37-2 for mouse Id-1 was calculated as $2.9 \times 10^{11}$. The equilibrium association constant for human Id-1 was calculated as $2.9 \times 10^9$.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications can be made therein without departing from the scope of the present invention as set forth in the claims. To particularly point out and distinctly claim the subject matter regarded as invention, the following claims conclude the specification.

What is claimed is:

1. A rabbit monoclonal antibody that binds to human Id1 protein, wherein the variable light chain of the antibody comprises the sequence of SEQ ID NO: 10, and the variable heavy chain of the antibody comprises the sequence of SEQ ID NO: 12.

2. A rabbit monoclonal antibody that binds to human Id1 protein and mouse Id1 protein, wherein the variable light chain of the antibody comprises the sequence of SEQ ID NO: 14, and the variable heavy chain of the antibody comprises the sequence of SEQ ID NO: 16.

3. A rabbit monoclonal antibody that binds to mouse Id1 protein, wherein the variable light chain of the antibody comprises the sequence of SEQ ID NO: 6, and the variable heavy chain of the antibody comprises the sequence of SEQ ID NO: 8.

4. A method of determining the concentration of human Id1 in a liquid sample, comprising the steps of:
   (a) reacting a liquid sample with the rabbit monoclonal antibody according to claim 1 or 2;
   (b) forming an immunocomplex between Id1 in the sample and the antibody; and
   (c) determining the concentration of the immunocomplex formed, whereby the concentration of human Id1 in the liquid sample is determined.

5. The method according to claim 4, wherein said reacting is contacting the sample with a solid-phase support having surface-attached human Id1 molecules in the presence of the rabbit monoclonal antibody that is labeled with a reporter molecule, wherein said surface-attached human Id1 is effective to compete with human Id1 in the sample for binding to the antibody.

6. A method of determining the concentration of mouse Id1 in a liquid sample, comprising the steps of:
   (a) reacting a liquid sample with the rabbit monoclonal antibody according to claim 2 or 3;
   (b) forming an immunocomplex between Id1 in the sample and the antibody, and
   (c) determining the concentration of the immunocomplex formed, whereby the concentration of mouse Id1 in the liquid sample is determined.

7. The method according to claim 6, wherein said reacting is contacting the sample with a solid-phase support having surface-attached mouse Id1 molecules in the presence of the rabbit monoclonal antibody that is labelled with a reporter molecule, wherein said surface-attached mouse Id1 is effective to compete with mouse Id1 in the sample for binding to the antibody.

8. A method of determining the concentration of human Id1 in a liquid sample, comprising the steps of:
   (a) reacting a liquid sample with a first antibody attached on a solid support and a second antibody in the liquid phase, wherein the first antibody and the second antibody binds to human Id1 at different epitopes and have no significant cross-reactivity against human Id2, Id3, or Id4;
   (b) forming an immunocomplex among Id1 in the sample, the first antibody, and the second antibody; and
   (c) determining the concentration of immunocomplex formed, wherein the first antibody or the second antibody is the rabbit monoclonal antibody according to claim 1 or 2, whereby the concentration of human Id1 in the liquid sample is determined.

9. A method of determining the concentration of mouse Id1 in a liquid sample, comprising the steps of:
   (a) reacting a liquid sample with a first antibody attached on a solid support and a second antibody in the liquid phase, wherein the first antibody and the second antibody binds to mouse Id1 at different epitopes and have no significant cross-reactivity against mouse Id2, Id3, or Id4;
   (b) forming an immunocomplex among Id1 in the sample, the first antibody, and the second antibody; and
   (c) determining the concentration of the immunocomplex formed, wherein the first antibody or the second antibody is the rabbit monoclonal antibody according to claim 2 or 3, whereby the concentration of mouse Id1 in the liquid sample is determined.

10. A method of detecting Id1 in a tissue sample by immunohstochemistry, comprising the steps of:
    (a) reacting a tissue sample with the rabbit monoclonal antibody according to claim 1, 2, or 3;
    (b) forming an immunocomplex between Id1 in the tissue sample and the antibody; and
    (c) detecting the immunocomplex formed by staining, whereby the Id1 in the tissue sample is detected.

11. The method according to claim 10, wherein the immunocomplex is detected by binding to a labeled secondary antibody.

12. A method for detecting Id1 in a sample, comprising:
    (a) applying a sample on gel;
    (b) performing gel electrophoresis and separating proteins in the sample by molecular weight;
    (c) transferring the proteins out of the gel and onto a membrane;
    (d) reacting the membrane with the rabbit monoclonal antibody according to claim 1, 2, or 3; wherein the antibody forms an immunocomplex with Id1 in the sample; and
    (e) detecting the immunocomplex, whereby the Id1 in the sample is detected.

13. The method according to claim 12, wherein the immunocomplex is detected by binding to a labeled secondary antibody.

* * * * *

SEQUENCE LISTING

```
<160> NUMBER OF SEQ ID NOS: 16

<210> SEQ ID NO 1
<211> LENGTH: 468
<212> TYPE: DNA
<213> ORGANISM: human

<400> SEQUENCE: 1
atgaaagtcg ccagtggcag caccgccacc gccgccgcgg gccccagctg cgcgctgaag        60
gccggcaaga cagcgagcgg tgcgggcgag gtggtgcgct gtctgtctga gcagagcgtg       120
gccatctcgc gctgcgccgg gggcgccggg gcgcgcctgc ctgccctgct ggacgagcag       180
caggtaaacg tgctgctcta cgacatgaac ggctgttact cacgcctcaa ggagctggtg       240 cccacccctgc cccagaaccg caaggtgagc aaggtggaga ttctccagca cgtcatcgac      300
tacatcaggg accttcagtt ggagctgaac tcggaatccg aagttggaac ccccgggggc       360
cgagggctgc cggtccgggc tccgctcagc accctcaacg gcgagatcag cgccctgacg       420
gccgaggcgg catgcgttcc tgcggacgat cgcatcttgt gtcgctga                   468

<210> SEQ ID NO 2
<211> LENGTH: 155
<212> TYPE: PRT
<213> ORGANISM: human

<400> SEQUENCE: 2

Met Lys Val Ala Ser Gly Ser Thr Ala Thr Ala Ala Ala Gly Pro Ser
1               5                   10                  15

Cys Ala Leu Lys Ala Gly Lys Thr Ala Ser Gly Ala Gly Glu Val Val
                20                  25                  30

Arg Cys Leu Ser Glu Gln Ser Val Ala Ile Ser Arg Cys Ala Gly Gly
            35                  40                  45

Ala Gly Ala Arg Leu Pro Ala Leu Leu Asp Glu Gln Gln Val Asn Val
        50                  55                  60
```

```
Leu Leu Tyr Asp Met Asn Gly Cys Tyr Ser Arg Leu Lys Glu Leu Val
 65                  70                  75                  80

Pro Thr Leu Pro Gln Asn Arg Lys Val Ser Lys Val Glu Ile Leu Gln
                 85                  90                  95

His Val Ile Asp Tyr Ile Arg Asp Leu Gln Leu Glu Leu Asn Ser Glu
            100                 105                 110

Ser Glu Val Gly Thr Pro Gly Gly Arg Gly Leu Pro Val Arg Ala Pro
        115                 120                 125

Leu Ser Thr Leu Asn Gly Glu Ile Ser Ala Leu Thr Ala Glu Ala Ala
    130                 135                 140

Cys Val Pro Ala Asp Asp Arg Ile Leu Cys Arg
145                 150                 155
```

<210> SEQ ID NO 3
<211> LENGTH: 447
<212> TYPE: DNA
<213> ORGANISM: Mus musculus

<400> SEQUENCE: 3

```
atgaaggtcg ccagtggcag tgccgcagcc gctgcaggcc ctagctgttc gctgaaggcg      60
ggcaggacag cgggcgaggt ggtacttggt ctgtcggagc aaagcgtggc catctcgcgc     120
tgcgctggga cgcgcctgcc cgccttgctg gacgagcagc aggtgaacgt cctgctctac     180
gacatgaacg gctgctactc acgcctcaag gagctggtgc ccaccctgcc cagaaccgc      240
aaagtgagca aggtggagat cctgcagcat gtaatcgact acatcaggga cctgcagctg     300
gagctgaact cggagtctga agtcgggacc accggaggcc ggggactgcc tgtccgcgcc     360
ccgctcagca ccctgaacgg cgagatcagt gccttggcgg ccgaggcggc atgtgttcca     420
gccgacgatc gcatcttgtg tcgctga                                         447
```

<210> SEQ ID NO 4
<211> LENGTH: 148
<212> TYPE: PRT
<213> ORGANISM: Mus musculus

<400> SEQUENCE: 4

```
Met Lys Val Ala Ser Gly Ser Ala Ala Ala Ala Ala Gly Pro Ser Cys
  1               5                  10                  15

Ser Leu Lys Ala Gly Arg Thr Ala Gly Glu Val Val Leu Gly Leu Ser
                 20                  25                  30

Glu Gln Ser Val Ala Ile Ser Arg Cys Ala Gly Thr Arg Leu Pro Ala
             35                  40                  45

Leu Leu Asp Glu Gln Gln Val Asn Val Leu Leu Tyr Asp Met Asn Gly
     50                  55                  60

Cys Tyr Ser Arg Leu Lys Glu Leu Val Pro Thr Leu Pro Gln Asn Arg
 65                  70                  75                  80

Lys Val Ser Lys Val Glu Ile Leu Gln His Val Ile Asp Tyr Ile Arg
                 85                  90                  95

Asp Leu Gln Leu Glu Leu Asn Ser Glu Ser Glu Val Gly Thr Thr Gly
            100                 105                 110

Gly Arg Gly Leu Pro Val Arg Ala Pro Leu Ser Thr Leu Asn Gly Glu
        115                 120                 125

Ile Ser Ala Leu Ala Ala Glu Ala Ala Cys Val Pro Ala Asp Asp Arg
    130                 135                 140

Ile Leu Cys Arg
```

<210> SEQ ID NO 5
<211> LENGTH: 336
<212> TYPE: DNA
<213> ORGANISM: Oryctolagus cuniculus

<400> SEQUENCE: 5

```
cgagtgctga cccagactgc atccccgtg tctgcggctg ttggaggcac agtcaccatc        60
aattgccagg ccagtcagag tgtttataat ggcaaccggt taggctggta tcagctgaaa      120
ccagggcagt ctcccaagga actgatccat gatgcatcca ctctggcatc tggggtccca      180
tcgcggttta gaggcagtgg atctgggacg cagttcactc tcaccatcaa cgacgtgcag      240
tgtgacgatg ctgccaccta ctactgtgta ggcagttatg cctgtagtac tggtgattgt      300
aatgttttcg gcggagggac cgaggtggtg gtcaaa                               336
```

<210> SEQ ID NO 6
<211> LENGTH: 112
<212> TYPE: PRT
<213> ORGANISM: Oryctolagus cuniculus

<400> SEQUENCE: 6

```
Arg Val Leu Thr Gln Thr Ala Ser Pro Val Ser Ala Ala Val Gly Gly
1               5                   10                  15
Thr Val Thr Ile Asn Cys Gln Ala Ser Gln Ser Val Tyr Asn Gly Asn
            20                  25                  30
Arg Leu Gly Trp Tyr Gln Leu Lys Pro Gly Gln Ser Pro Lys Glu Leu
        35                  40                  45
Ile His Asp Ala Ser Thr Leu Ala Ser Gly Val Pro Ser Arg Phe Arg
    50                  55                  60
Gly Ser Gly Ser Gly Thr Gln Phe Thr Leu Thr Ile Asn Asp Val Gln
65                  70                  75                  80
Cys Asp Asp Ala Ala Thr Tyr Tyr Cys Val Gly Ser Tyr Ala Cys Ser
                85                  90                  95
Thr Gly Asp Cys Asn Val Phe Gly Gly Gly Thr Glu Val Val Val Lys
            100                 105                 110
```

<210> SEQ ID NO 7
<211> LENGTH: 330
<212> TYPE: DNA
<213> ORGANISM: Oryctolagus cuniculus

<400> SEQUENCE: 7

```
cagtcggtgg aggagtccgg gggtcgcctg gtcacgcctg gacacccct gacactcacc        60
tgcaaagtct ctggattcga catcaatagc tatgcaatgg actggttccg ccaggctcca     120
gggaaggggc tggaatggat cggaatgatg tctactcgtg gtaatacata ctacacgagc     180
tgggcgaaag gccgcttcac catctccaaa acctcgtcga ccacggtgga tctgaaaatg     240
accagtctga aaccgagga cacggccact tatttctgtg ccagagggggg cttgtggggc     300
ccaggcaccc tggtcaccgt ctcctccgga                                      330
```

<210> SEQ ID NO 8
<211> LENGTH: 110
<212> TYPE: PRT
<213> ORGANISM: Oryctolagus cuniculus

<400> SEQUENCE: 8

```
Gln Ser Val Glu Glu Ser Gly Gly Arg Leu Val Thr Pro Gly Thr Pro
1               5                   10                  15

Leu Thr Leu Thr Cys Lys Val Ser Gly Phe Asp Ile Asn Ser Tyr Ala
            20                  25                  30

Met Asp Trp Phe Arg Gln Ala Pro Gly Lys Gly Leu Glu Trp Ile Gly
        35                  40                  45

Met Met Ser Thr Arg Gly Asn Thr Tyr Tyr Thr Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Gly Leu Trp Gly Pro Gly Thr Leu Val Thr Val Ser Ser Gly
            100                 105                 110

<210> SEQ ID NO 9
<211> LENGTH: 333
<212> TYPE: DNA
<213> ORGANISM: Oryctolagus cuniculus

<400> SEQUENCE: 9
gtattcgaat tgacccagac tccagcctcc gtggaggcag ctgtgggagg cacagtcacc    60
atcaagtgcc aggccagtca gagcattagt agctacttag cctggtatca gcagaaacca   120
ggacagcctc ccaagctcct ggtctacagc gcatccactc tgcaatctgg ggtcccatcg   180
cggttcaaag gcagtggatc tgggacagac ttcactctca ccatcagcgg cgtgcagtgt   240
gacgatgctg ccacttacta ctgtcaaagt tattatgatg gtagtagtac ttctggtaat   300
gttttcggcg agggaccga ggtggtggtc aag                                 333

<210> SEQ ID NO 10
<211> LENGTH: 111
<212> TYPE: PRT
<213> ORGANISM: Oryctolagus cuniculus

<400> SEQUENCE: 10

Val Phe Glu Leu Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Val
        35                  40                  45

Tyr Ser Ala Ser Thr Leu Gln Ser Gly Val Pro Ser Arg Phe Lys Gly
    50                  55                  60

Ser Gly Ser Gly Thr Asp Phe Thr Leu Thr Ile Ser Gly Val Gln Cys
65                  70                  75                  80

Asp Asp Ala Ala Thr Tyr Tyr Cys Gln Ser Tyr Tyr Asp Gly Ser Ser
                85                  90                  95

Thr Ser Gly Asn Val Phe Gly Gly Gly Thr Glu Val Val Val Lys
            100                 105                 110

<210> SEQ ID NO 11
<211> LENGTH: 375
<212> TYPE: DNA
<213> ORGANISM: Oryctolagus cuniculus

<400> SEQUENCE: 11
cagtcgttgg aggagtccgg gggagacctg gtcaagcctg ggcatccct gacactcacc    60
```

```
tgcacagcct ctggattctc cttcagtatc agctactata tgtgctgggt ccgccaggct   120
ccagggaagg ggccggagtg gatcggatgt attattactg gtaatattgt cggcacttac   180
tacgaaaact gggcgaaagg ccgattcacc atctccaaaa cctcgagcac ggtgactctg   240
caaatgacca gtctgacagc cgcggacacg gccacctatt tttgtgcgag aggatctggt   300
agtgctagtg ctgattatat tgggatttac tttaagttgt ggggcccagg cacccctggtc  360 accgtctcct caggg                                                    375
```

<210> SEQ ID NO 12
<211> LENGTH: 125
<212> TYPE: PRT
<213> ORGANISM: Oryctolagus cuniculus

<400> SEQUENCE: 12

```
Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ile Ser Tyr
                20                  25                  30

Tyr Met Cys Trp Val Arg Gln Ala Pro Gly Lys Gly Pro Glu Trp Ile
            35                  40                  45

Gly Cys Ile Ile Thr Gly Asn Ile Val Gly Thr Tyr Tyr Glu Asn Trp
        50                  55                  60

Ala Lys Gly Arg Phe Thr Ile Ser Lys Thr Ser Ser Thr Val Thr Leu
65                  70                  75                  80

Gln Met Thr Ser Leu Thr Ala Ala Asp Thr Ala Thr Tyr Phe Cys Ala
                85                  90                  95

Arg Gly Ser Gly Ser Ala Ser Ala Asp Tyr Ile Gly Ile Tyr Phe Lys
            100                 105                 110

Leu Trp Gly Pro Gly Thr Leu Val Thr Val Ser Ser Gly
        115                 120                 125
```

<210> SEQ ID NO 13
<211> LENGTH: 330
<212> TYPE: DNA
<213> ORGANISM: Oryctolagus cuniculus

<400> SEQUENCE: 13

```
gctgacattg tgatgaccca gactccagcc tccgtggagg cagctgtggg aggcacagtc   60
accatcaagt gccaggccag tgagagcatt attaatagat tagcctggta tcagcagaaa   120
ccagggcagc ctcccaagct cctgatctac agggcatcca ctctggaatc tggggtccca   180
tcgcggttca aaggcagtgg atctgggaca gagttcactc tcaccatcag cgacctggag   240
tgtgacgatg gtgccactta ctattgtcaa gctactgact atggtgatag ttatttttact  300 ttcggcggag ggaccgaggt ggtggtcaaa                                    330
```

<210> SEQ ID NO 14
<211> LENGTH: 110
<212> TYPE: PRT
<213> ORGANISM: Oryctolagus cuniculus

<400> SEQUENCE: 14

```
Ala Asp Ile Val Met Thr Gln Thr Pro Ala Ser Val Glu Ala Ala Val
1               5                   10                  15

Gly Gly Thr Val Thr Ile Lys Cys Gln Ala Ser Glu Ser Ile Ile Asn
                20                  25                  30
```

```
Arg Leu Ala Trp Tyr Gln Gln Lys Pro Gly Gln Pro Pro Lys Leu Leu
        35                  40                  45
Ile Tyr Arg Ala Ser Thr Leu Glu Ser Gly Val Pro Ser Arg Phe Lys
 50                  55                  60
Gly Ser Gly Ser Gly Thr Glu Phe Thr Leu Thr Ile Ser Asp Leu Glu
 65                  70                  75                  80
Cys Asp Asp Gly Ala Thr Tyr Tyr Cys Gln Ala Thr Asp Tyr Gly Asp
                 85                  90                  95
Ser Tyr Phe Thr Phe Gly Gly Gly Thr Glu Val Val Val Lys
                100                 105                 110

<210> SEQ ID NO 15
<211> LENGTH: 351
<212> TYPE: DNA
<213> ORGANISM: Oryctolagus cuniculus

<400> SEQUENCE: 15
cagtcggtgg aggagtccgg gggtcgcctg gtctcgcctg ggacacccct gacactcacc      60
tgcacagtct ctggattctc cctcagttct tttccaatgg gctgggtccg ccaggctcca    120
gggaaggggc tggaatacat cggaatcatg agtactagtg gtagcacata ctacgcggac    180
tgggcgaaag gccgattcac catctccaaa acctcgtcga ccacgatgga tctgaaaatg    240
accagtctga aaccgaggac acggccacc tatttctgtg ccagagggc tgctagtagg      300 ttttatgcct taccttgtg gggcccaggc accctggtca ccgtctcctc a               351

<210> SEQ ID NO 16
<211> LENGTH: 117
<212> TYPE: PRT
<213> ORGANISM: Oryctolagus cuniculus

<400> SEQUENCE: 16

Gln Ser Val Glu Glu Ser Gly Gly Arg Leu Val Ser Pro Gly Thr Pro
 1               5                  10                  15
Leu Thr Leu Thr Cys Thr Val Ser Gly Phe Ser Leu Ser Ser Phe Pro
                20                  25                  30
Met Gly Trp Val Arg Gln Ala Pro Gly Lys Gly Leu Glu Tyr Ile Gly
         35                  40                  45
Ile Met Ser Thr Ser Gly Ser Thr Tyr Tyr Ala Asp Trp Ala Lys Gly
 50                  55                  60
Arg Phe Thr Ile Ser Lys Thr Ser Ser Thr Thr Met Asp Leu Lys Met
 65                  70                  75                  80
Thr Ser Leu Thr Thr Glu Asp Thr Ala Thr Tyr Phe Cys Ala Arg Gly
                 85                  90                  95
Ala Ala Ser Arg Phe Tyr Ala Phe Thr Leu Trp Gly Pro Gly Thr Leu
                100                 105                 110
Val Thr Val Ser Ser
            115
```